United States Patent
Yabuki et al.

(10) Patent No.: US 7,981,686 B2
(45) Date of Patent: Jul. 19, 2011

(54) INDICATOR FOR ASSESSING BODY ODOR, PROCESS FOR PRODUCING THE SAME, BODY ODOR ASSESSMENT METHOD, METHOD OF ASSESSING EFFICACIOUSNESS OF DEODORANT AND KIT FOR CONVENIENTLY ASSESSING BODY ODOR

(75) Inventors: Masayuki Yabuki, Tokyo (JP); Yoshihiro Hasegawa, Tokyo (JP); Masamoto Matsukane, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/750,090

(22) Filed: Mar. 30, 2010

(65) Prior Publication Data

US 2010/0184122 A1    Jul. 22, 2010

Related U.S. Application Data

(62) Division of application No. 10/529,897, filed on Dec. 16, 2005, now abandoned.

(30) Foreign Application Priority Data

| Oct. 4, 2002 | (JP) | 2002-293104 |
| Mar. 25, 2003 | (JP) | 2003-083801 |
| Apr. 22, 2003 | (JP) | 2003-116582 |
| Jun. 4, 2003 | (JP) | 2003-160082 |
| Oct. 6, 2003 | (JP) | 2003-346586 |

(51) Int. Cl.
*G01N 33/00* (2006.01)

(52) U.S. Cl. ......... 436/120; 436/119; 436/129; 436/166

(58) Field of Classification Search .......... 436/119–120, 436/129, 166
See application file for complete search history.

(56) References Cited

U.S. PATENT DOCUMENTS

| 4,053,630 A | * | 10/1977 | Yu et al. ................ 514/502 |
| 6,129,941 A | * | 10/2000 | Escher et al. ........... 426/535 |
| 7,264,956 B2 | | 9/2007 | Natsch et al. |
| 2003/0100842 A1 | | 5/2003 | Rosenberg et al. |

FOREIGN PATENT DOCUMENTS

DE    23 16 456    10/1973

(Continued)

OTHER PUBLICATIONS

Andreas Schmidt, "Römpp Online", Thieme Chemistry, XP002526669, Aug. 2006, pp. 1-3.

(Continued)

*Primary Examiner* — Michael A Marcheschi
*Assistant Examiner* — Jameson Q Ma
(74) *Attorney, Agent, or Firm* — Oblon, Spivak, McClelland, Maier & Neustadt, L.L.P.

(57) ABSTRACT

A method of assessing body odor using as an index an indicator material comprising an alcohol compound having a mercapto group at the 3-position represented by the following formula (2) and/or a substance that is a derivative of an alcohol compound having a mercapto group at the 3-position, wherein an atom(s) or an atom group(s) is introduced to a mercapto group and/or a hydroxyl group of an alcohol compound having a mercapto group at the 3-position represented by the formula (2):

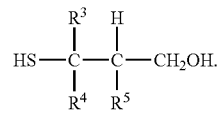

21 Claims, 11 Drawing Sheets

Total ion chromatogram of volatile components in incubated perspiration of a person having an apocrine odor

FOREIGN PATENT DOCUMENTS

| | | |
|---|---|---|
| JP | 10-25265 | 1/1998 |
| JP | 2000-95753 | 4/2000 |
| JP | 2001-2634 | 1/2001 |
| JP | 2003-12637 | 1/2003 |

OTHER PUBLICATIONS

"Hexanoic acid, 3-hydroxy-3-methyl", XP002526670, Database accession No. RN: 58888-76-9, Nov. 16, 1984, Abstract.

"Hydrazine,(2-nitrophenyl)", XP002526671, Database accession No. RN: 3034-19-3, Nov. 16, 1984, Abstract.

"9-Anthracenecarboxaldehyde, one", XP 002526672, Database accession No. RN: 10401-59-9, Nov. 16, 1984, Abstract.

F. Kanda, et al., "Elucidation of chemical compounds responsible for foot malodour", British Journal of Dermatology, vol. 122, Jan. 1, 1990, pp. 771-776.

Chenhui Zeng, A human axillary odorant is carried by apolipoprotein D, Proceedings of the National Academy of Sciences of the United States of America, vol. 93, pp. 6626-6630, Jun. 25, 1996.

P.J. Rennie, In-vitro and in-vivo studies of human axillary odour and the cutaneous microflora, British Journal of Dermatology, vol. 124, pp. 596-602, Dec. 18, 1991.

Andreas Natsch, A Apecific Bacterial Aminoaxylase Cleaves Odorant Precursors Secreted in Human Axilla, The Journal of Biological Chemistry, vol. 278, No. 8, pp. 5718 to 5727, Feb. 21, 2003.

"Aji To Nidi No Bunshininshiki" (Molecular perception of taste and smell), Survey of Chemistry, Quarterly, No. 40, pp. 205-211, 1999.

Hör et al., Absolute configurational assignment of acyclic hydroxyl carboxylic acids: a new strategy in exciton-coupled circular dichroism, J. Org. Chem. vol. 63, pp. 322-325. (1998).

Yabuki et al. The study of human body odor. A new odorant found in axillae. Koryo, Terupen oyobi Seiyu Kagaku ni kansuru Toronkai Koen Yoshishu. pp. 124-126. (2002).

Labows et al. Axillary odor: determination, formation and control. Antiperspirants and Deodorants. $2^{nd}$ Edition. Cosmetic Science and Technology Series vol. 20. pp. 59-82. (1999).

* cited by examiner

Total ion chromatogram of an acid extract of perspiration of a person having an apocrine odor Total ion chromatogram of an acid extract of perspiration of a person having no apocrine odor Relationship between 3-hydroxy-3-methylhexanoic acid and an apocrine odor Total ion chromatogram of volatile components in perspiration of a person having an apocrine odor Total ion chromatogram of volatile components in perspiration of a person having no apocrine odor Total ion chromatogram of volatile components in incubated perspiration of a person having an apocrine odor Total ion chromatogram of volatile components in incubated perspiration of a person having no apocrine odor Quick and convenient method for examining body odor utilizing the coloration reaction Example (1) of how kit for conveniently accessing body odor is used <If positive>

<If negative>

Example (2) of how kit for conveniently accessing body odor is used

Relationship between strength of apocrine odor and color differences

Absorbance of methanol fraction and ether fraction

INDICATOR FOR ASSESSING BODY ODOR, PROCESS FOR PRODUCING THE SAME, BODY ODOR ASSESSMENT METHOD, METHOD OF ASSESSING EFFICACIOUSNESS OF DEODORANT AND KIT FOR CONVENIENTLY ASSESSING BODY ODOR

The present application is a divisional of U.S. patent application Ser. No. 10/529,897, filed Dec. 16, 2005, now abandoned, the contents of which are incorporated herein in their entirety by reference.

TECHNICAL FIELD

The present invention relates to an indicator material for assessing a body odor, and a method for assessing a level of a body odor or effectiveness of a deodorant.

Also, the present invention relates to an assessing kit and an assessment method including a coloration reagent, which reacts β-hydroxycarboxylic acid or the like originated from perspiration of a human with the coloration reagent.

BACKGROUND ART

Recently, number of people who are anxious about their body odor is increasing according to the growing desire for hygiene. The body odor is a collective term for an odor generated from any parts of a body, mainly a head, a mouth, underarms, a genital area, feet or the like. Particularly, since an axillary odor (odor of underarms) is easily sensed by a person oneself or people around, a level thereof, for instance, some factors including the presence, strength, difference in quality or the like of the axillary odor tends to dominate the level of body odor in terms of a whole body. Further, the person oneself or people around often feels the axillary odor itself uncomfortable rather than the body odor.

In the axillary region of a human, there are not only eccrine glands distributed almost all over the body but also peculiar sweat glands called as apocrine glands. The axillary region of a human is a part in which perspiration is less likely to vaporize and bacteria are likely to grow. Hence, it is likely that perspiration secreted from two kinds of sweat glands (eccrine sweat and apocrine sweat), sebum, scurf or the like are metabolized by bacteria on the skin to produce an odor.

An odor due to an eccrine sweat is called as a lower fatty acid odor or simply an acid odor, which is caused by a lower carboxylic acid having 2 to 5 carbons and smells sour and stuffy (hereinafter called as a lower fatty acid odor or an acid odor). Also, such an odor is not only produced in the underarm but also in all skin surfaces of the whole body. On the other hand, an odor derived from the apocrine sweat is produced in an axillary region of a human having so called tragomaschalia habitus and called as an apocrine odor or simply an "axillary odor" to distinguish. The apocrine odor is a pungent odor peculiar to an axillary region and particularly easily sensed by a person oneself or people around. There are individual differences in actual axillary odors, which can be roughly classified into an acid odor, an apocrine odor and the mixed odor thereof.

The people of tragomaschalia habitus tend to have more apocrine glands in the axillary region wherein an acid odor due to an eccrine sweat and an apocrine odor are mixed to produce a strong peculiar odor. Thus, if a person is anxious about own axillary odor, the person tries to reduce the odor by using a deodorant having a deodorant effect or germicidal effect, or by removing apocrine glands of the axillary region in a surgical way if the apocrine odor is particularly strong.

Hence, people who are anxious about own body odor or axillary odor, people who have their body odor pointed out at home, school office or the like by others, or people who may place their underarms in front of someone's face such as hair stylists and dentists even if their odors are in unnoticeable level by themselves have great interest in how much apocrine odor they originally have in their axillary regions, and further whether the use of deodorants or the effort to reduce a body odor such as an operation to remove apocrine glands is currently effective.

Conventionally, as methods of assessing a body odor, particularly an apocrine odor, there are: (1) an organoleptic test wherein a third party smells to determine an odor of perspiration of axillary regions with one's nose; (2) an empirical assessing method which presumes from the facts which are considered to be relative to an apocrine odor such as genetic information, e.g. whether there is a family member having tragomaschalia habit, a wet cerumen, coloring of an underwear in the axillary regions or the like; (3) a method which presumes from number and size of apocrine glands, or the like.

The method (1) needs professional panel members such as a skilled dermatologist, thus, it cannot be easily performed. Also, the method (1) assesses the level of apocrine odor by smelling an odor of the cotton wool which wiped underarms of a test subject, which allows to mingle a judgment with a large degree of the assessor's subjectivity and has difficulty in a quantitative evaluation. Further, when the evaluation is performed consecutively, a sense of smell may get tired so as to lower objectivity.

The method (2) judges from genetic potential or indirectly judges from a relationship between a wet cerumen and an apocrine odor. The assessment by coloring of underwear focuses on coloring matter contained in perspiration of apocrine glands, which does not directly evaluate the apocrine odor of axillary regions, thus, it is an indirect assessment method.

Therefore, there is a risk of false assessment with limited evaluation points and there is a possibility of ignoring axillary odor which is not actualized. Also, such studies can be rough indications for assessing tragomaschalia habit, however, since they are not quantitative and hard to assess, they may lack accuracy and be not practical to assess the improvement in axillary odor after the operation to remove apocrine glands, the presence and level of recurrence of apocrine odor due to regeneration of apocrine glands after the operation, the effectiveness of deodorizing or masking of a deodorant or the like.

The method (3) estimates a level of a body odor in such manner that a doctor makes a surgical incision in axillary regions and then observes number and size of apocrine glands. A test subject needs to accept mental and physical suffering, thus, the method cannot be easily performed. Also, the operation fee is generally high.

Trans-3-methyl-2-hexenoic acid, 7-octenoic acid or the like contained in perspiration of underarms as odor components which are distinctive of underarms is disclosed in "Molecular Recognition of Taste and Smell," Kagaku Sosetsu No. 40, 205-211, (1999). An use of certain β-hydroxycarboxylic acid or the salt thereof as an animal perfume material is disclosed in Japanese Patent Application Laid-Open (JP-A) No. Hei. 10-25265.

On the other hand, a compound having a thiol group at the 3-position which has an effect to provide a significantly strong clary sage-like odor as a flavoring component is disclosed in JP-A No. 2000-95753.

3-Mercapto-3-methyl-hexane-1-ol and 3-mercapto-2-methyl-butane-1-ol are disclosed as alcohol compounds having a mercapto group at the 3-position in JP-A No. 2001-2634. They are disclosed as flavoring components having characteristics, wherein a S isomer of 3-mercapto-3-methyl-hexane-1-ol has a grass-like or, agrestic odor, a R isomer of 3-mercapto-3-methyl-hexane-1-ol has a grapefruit/passion fruit-like, currant-like or onion-like odor, and 3-mercapto-2-methyl-butane-1-ol has a grass-like, leek-like and gas-like odor.

3-Mercapto alcohol and formic and acetic esters thereof are disclosed in German Patent Application Laid-Open No. 2,316,456 as fragrance agents and flavor agents effective for preparation and modification of a wide range of flavor components, wherein said 3-mercapto alcohol and formic and acetic esters thereof have onion-like, sulfur-like or sweat-like odor.

A thio derivative used as a flavor component and/or a flavor enhancer is disclosed in JP-A No. 2003-12637, wherein the thio derivative reminds of smell of a blackcurrant, onion or grapefruit.

However, none of β-hydroxycarboxylic acid and/or derivative thereof and the alcohol compounds having a mercapto group at the 3-position and/or derivatives thereof was recognized to have a relationship with a body odor of a human particularly in terms of a causative agent of a body odor or a constituent of an axillary odor of a human. Hence, presence or strength of a body odor of a human, particularly, an apocrine odor of axillary regions has not been able to be assessed objectively and quantitatively.

Also, as a characteristic component of the apocrine odor in axillary regions of a human, there were conventionally not only unsaturated carboxylic acid having 6 to 10 carbons as typified by trans-3-methyl-2-hexenoic acid and 7-octenoic acid but also lower carboxylic acid having 5 or less carbons which causes acid odor and higher carboxylic acid originated from sebum in mixture. It has been difficult to selectively separate the unsaturated carboxylic acid which is a characteristic component of an apocrine odor among the various acid components

DISCLOSURE OF INVENTION

An object of the present invention is to provide an indicator material for assessing body odor comprising at least one member selected from the group consisting of:

a substance (A) which is a β-hydroxycarboxylic acid compound represented by the following formula (1):

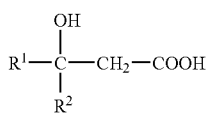

Formula (1)

wherein $R^1$ is an alkyl having 1 to 4 carbons; $R^2$ is a hydrogen atom or an alkyl having 1 to 4 carbons, and the total number of carbons in the formula (1) is 10 or less;

a substance (B) which is a derivative of β-hydroxycarboxylic acid, wherein an atom(s) or an atomic group(s) is introduced to a hydroxyl group and/or a carboxylic group of a β-hydroxycarboxylic acid compound represented by the formula (1);

a substance (C) which is an alcohol compound having a mercapto group at the 3-position represented by the following formula (2):

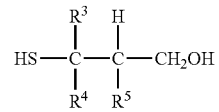

Formula (2)

wherein $R^3$ is a hydrogen atom or methyl group; $R^4$ is an alkyl group having 1 to 3 carbons; and $R^5$ is a hydrogen atom or a methyl group, the total number of carbons in the formula (2) is 8 or less; and a substance (D) which is a derivative of an alcohol compound having a mercapto group at the 3-position, wherein an atom(s) or an atom group (s) is introduced to a mercapto group and/or a hydroxyl group of an alcohol compound having a mercapto group at the 3-position represented by the formula (2).

The present invention provides an indicator material capable of assessing presence and strength of an apocrine odor of axillary regions about which many people are particularly anxious among body odors objectively and quantitatively, and a method using the indicator material to assess a level of a body odor or effectiveness of a deodorant. Also, the present invention provides a method of producing the indicator material for a simple and accurate assessment of a body odor. Further, the present invention provides a kit capable of surely, promptly and easily assessing the kind and level of body odor of a human, and a method of assessing human odor using the kit.

As the result of diligent researches on components which cause the apocrine odor contained in perspiration of underarms, the inventors found out that substances exist in perspiration which have a significantly similar odor to the apocrine odor and characteristically exist in perspiration of people having the apocrine odor, have enough concentration to accurately determine the quantity as they are or by incubation, and can be separated by a simple chemical operation. Further, the inventors made the substances capable of being used as objective indexes for quantitatively assessing a level of the apocrine odor of axillary regions.

Also, various marker materials can be introduced to such substances in order to increase analytical sensitivity and/or accuracy of assessment, and obtained derivatives of indicator materials can be suitably used for assessing body odor and effectiveness of a deodorant.

According to the present invention, an indicator material for assessing body odor is comprised of at least one member selected from the group consisting of:

a substance (A) which is a β-hydroxycarboxylic acid compound represented by the following formula (1):

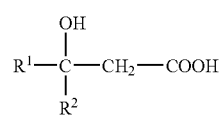

Formula (1)

wherein $R^1$ is an alkyl having 1 to 4 carbons; $R^2$ is a hydrogen atom or an alkyl having 1 to 4 carbons, and the total number of carbons in the formula (1) is 10 or less;

a substance (B) which is a derivative of β-hydroxycarboxylic acid, wherein an atom (s) or an atomic group (s) is introduced to a hydroxyl group and/or a carboxylic group of a β-hydroxycarboxylic acid compound represented by the formula (1);

a substance (C) which is an alcohol compound having a mercapto group at the 3-position represented by the following formula (2):

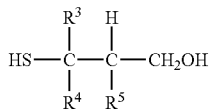

Formula (2)

wherein $R^3$ is a hydrogen atom or methyl group; $R^4$ is an alkyl group having 1 to 3 carbons; and $R^5$ is a hydrogen atom or a methyl group, provided that the total number of carbons in the formula (2) is 8 or less; and a substance (D) which is a derivative of an alcohol compound having a mercapto group at the 3-position, wherein an atom(s) or an atom group (s) is introduced to a mercapto group and/or a hydroxyl group of an alcohol compound having a mercapto group at the 3-position represented by the formula (2).

Also, a method of assessing body odor and a method of assessing effectiveness of a deodorant according to the present invention are methods of assessing the level of body odor or effectiveness of a deodorant using as an indicator material at least one member selected from the group consisting of the above-mentioned substances (A), (B), (C) and (D). In the case of selecting two or more indicator substances among the substances (A), (B), (C) and (D) to use, an indicator material containing all selected substances may be used or each of the selected indicator substances may be used separately in the course of the assessment process. Also, in a set of assessment process, a part of selected indicator substances may be mixed to use and each of the substances which is not mixed may be used separately as a sole substance.

In the present invention, one kind among the above-mentioned substances (A), (B), (C), and (D) may be selected to use, or two or more kinds of indicator substances may be arbitrarily selected to use in combination. For example, the indicator substances may be used singly or in combination as follows.

(1) An indicator substance comprising at least one member selected from the group consisting of the substance (A) and/or the substance (B).

The substance (A), i.e. a β-hydroxycarboxylic acid compound represented by the formula (1), is particularly effective to evaluate a cumin oil-like apocrine odor. The substance (B) is a derivative of the substance (A) and suitably used in lieu of the substance (A) in order to increase analytical sensitivity and/or accuracy of assessment, wherein the substance (B) may be used in combination with the substance (A).

(2) An indicator substance comprising at least one member selected from the group consisting of the substance (C) and/or the substance (D).

The substance (C), i.e. an alcohol compound having a mercapto group at the 3-position represented by the formula (2), is particularly effective to evaluate a sulfur-like apocrine odor. The substance (D) is a derivative of the substance (C) and suitably used in lieu of the substance (C) in order to increase analytical sensitivity and/or accuracy of assessment, wherein the substance (D) may be used in combination with the substance (C).

(3) A combination of an indicator substance comprising at least one member selected from the group consisting of the substance (A) and/or the substance (B) and an indicator substance comprising at least one member selected from the group consisting of the substance (C) and/or the substance (D).

By using the indicator substance comprising the group consisting of the substance (A) and/or the substance (B) in combination with the indicator substance comprising the group consisting of the substance (C) and/or the substance (D), both cumin oil-like apocrine odor and sulfur-like apocrine odor can be evaluated, thus, an accurate evaluation can be performed in accordance with an actual apocrine odor.

(4) A combination of an indicator substance comprising at least one member selected from the group consisting of the substance (A) and an indicator substance comprising at least one member selected from the group consisting of the substance (C).

This is a combination of indicator substances which are not derivatized, which may be more suitable than using derivatives depending on a method of analysis or evaluation.

(5) A combination of an indicator substance comprising at least one member selected from the group consisting of the substance (B) and an indicator substance comprising at least one member selected from the group consisting of the substance (D).

This is a combination of indicator substances which are derivatized, which can analyze or evaluate a level of odor by methods other than a direct assessment using an organoleptic test and also can enhance analytical sensitivity and/or accuracy of assessment.

Moreover, a method of producing an indicator material according to the present invention is a method of producing an alcohol compound having a mercapto group at the 3-position represented by the formula (2) by incubating the perspiration originated from a human in an environment with 10 v/v % or less of an oxygen concentration.

The perspiration originated from a human is incubated in an environment with anaerobic or microaerophilic atmosphere to produce an alcohol compound having a mercapto group at the 3-position in large quantity, thereby, it is possible to make the assessment of body odor and effectiveness of a deodorant easier and more accurate.

Further, the present inventors have focused attention on a point that a level of apocrine odor can be easily assessed from the color exhibited by separating β-hydroxycarboxylic acid including 3-hydroxy-3-methylhexanoic acid which is newly found out as a main component which causes apocrine odor from perspiration of axillary regions, and thereafter reacting it with a coloration reagent, and developed a kit capable of surely and easily assessing a level of apocrine odor itself or a total body odor with focus on apocrine odor, and a method of assessing human odor using the kit.

The kit for assessing according to the present invention is a kit for assessing body odor of a human including a coloration reagent which reacts with β-hydroxycarboxylic acid and/or fatty acid having 12 or less carbons other than said β-hydroxycarboxylic acid originated from perspiration of a human respectively. The kit enabled to assess a kind and strength of odor and a level of human odor originated from perspiration of a human surely, promptly and easily from the color exhibited by reacting β-hydroxycarboxylic acid which is a material causing an apocrine odor and fatty acid having 12 or less carbons other than said β-hydroxycarboxylic acid which is a material causing an acid odor with a coloration reagent.

A first method of assessing body odor using the kit of the present invention is a method of assessing body odor of a human comprising steps of:

a first step of extracting a mixture of β-hydroxycarboxylic acid and fatty acid having 12 or less carbons other than said β-hydroxycarboxylic acid from perspiration of a human;

a second step of adding the reagent to the mixture to exhibit color; and a third step of assessing the kind and/or strength of body odor from the color exhibited in the second step.

Also, a second method of assessing body odor using the kit of the present invention is a method of assessing body odor of a human comprising steps of:

a first step of extracting a mixture of β-hydroxycarboxylic acid and fatty acid having 12 or less carbons other than said β-hydroxycarboxylic acid from perspiration of a human;

a second step of separating β-hydroxycarboxylic acid from the mixture;

a third step of reacting said β-hydroxycarboxylic acid separated in the second step with the reagent to exhibit color; and a fourth step of assessing the kind and/or strength of body odor from the color exhibited in the third step.

Further, a third method of assessing body odor using the kit of the present invention is a method of assessing body odor of a human comprising steps of:

a first step of extracting a mixture of β-hydroxycarboxylic acid and fatty acid having 12 or less carbons other than said β-hydroxycarboxylic acid from perspiration of a human;

a second step of separating the mixture into β-hydroxycarboxylic acid and fatty acid having 12 or less carbons other than said β-hydroxycarboxylic acid respectively;

a third step of reacting said β-hydroxycarboxylic acid separated in the second step with the reagent to exhibit color;

a fourth step of reacting said fatty acid having 12 or less carbons other than said β-hydroxycarboxylic acid separated in the second step with the reagent to exhibit color;

a fifth step of assessing the kind and/or strength of body odor from each of the colors exhibited in the third and fourth steps.

BRIEF DESCRIPTION OF DRAWINGS

In the accompanying drawings.

BEST MODE FOR CARRYING OUT THE INVENTION

Hereinafter, the present invention will be explained in detail. Contents of all publications cited in the present specification are incorporated herein by reference.

According to the present invention, an indicator material for assessing body odor which is quite similar to actual apocrine odor is prepared by selecting one or more substances among a group of β-hydroxycarboxylic acid compounds including 3-hydroxy-3-methylhexanoic acid and compounds having a chemical structure quite similar thereto, or selecting one or more substances among a group of 3-mercapto alcohol compounds including 3-mercapto-3-methylhexanol and compounds having a chemical structure quite similar thereto, or preferably by using the β-hydroxycarboxylic acid compound and the 3-mercapto alcohol compound in combination, and thus an accurate evaluation result with regard to the level (strength and quality) of body odor which people actually feel and effectiveness of a deodorant against body odor can be obtained.

It is considered that said 3-hydroxy-3-methylhexanoic acid and 3-mercapto alcohol compounds found in perspiration of axillary regions of a human by the inventors of the present invention have the following features, thus, the presence amount and the presence state of 3-hydroxy-3-methylhexanoic acid and/or 3-mercapto alcohol compounds in axillary regions form the level and the individual difference of apocrine odor.

(Features of 3-hydroxy-3-methylhexanoic Acid and 3-mercapto alcohol Compound)

(1) A person that 3-hydroxy-3-methylhexanoic acid and/or 3-mercapto alcohol compound is not detected in the perspiration of his axillary regions does not have the apocrine odor, but a person that the 3-hydroxy-3-methylhexanoic acid and/or 3-mercapto alcohol compound is detected in his perspiration of the axillary regions has the apocrine odor. That is, the 3-hydroxy-3-methylhexanoic acid and 3-mercapto alcohol compound are specifically present in the person who has the apocrine odor (FIGS. 1, 2, 4, and 5).

(2) The apocrine odor is stronger in a person who has more 3-hydroxy-3-methylhexanoic acid (FIG. 3) and/or 3-mercapto alcohol compound contained in the perspiration of the axillary regions.

Figure 6:
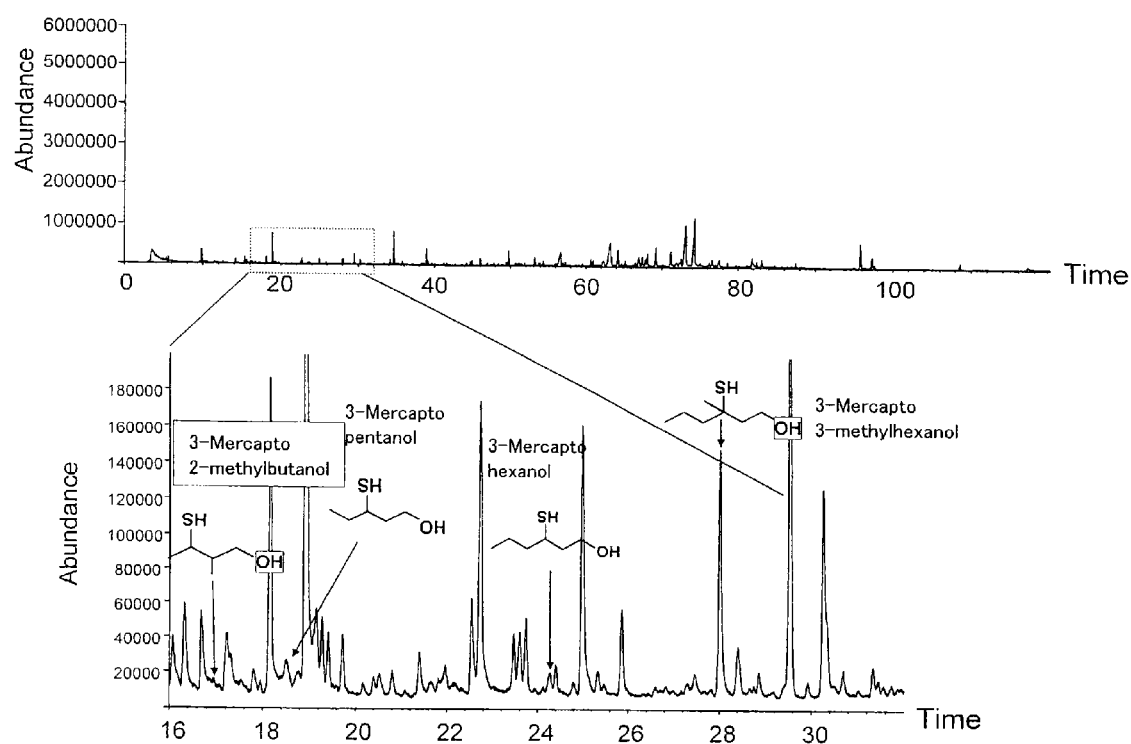
FIG. 6 shows the result of GC-MS analysis of the perspiration of a person having apocrine odor after incubation.
Figure 7:
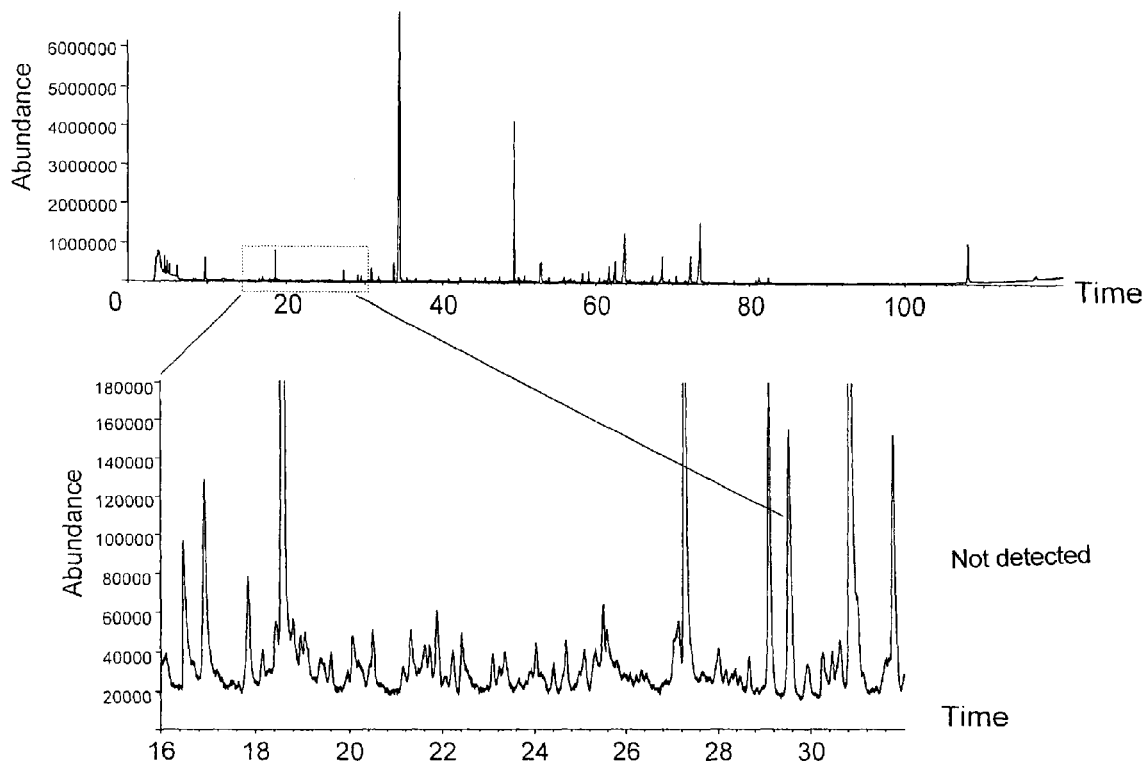
FIG. 7 shows the result of GC-MS analysis of the perspiration of a person not having apocrine odor after incubation.

(3) A person that 3-hydroxy-3-methylhexanoic acid and/or 3-mercapto alcohol compound is not detected in the perspiration of his axillary regions even after incubation does not have the apocrine odor. On the other hand, as for a person having the apocrine odor, the amount of 3-hydroxy-3-methylhexanoic acid and/or the 3-mercapto alcohol compound contained in the perspiration of his axillary regions increases by incubation. That is, 3-hydroxy-3-methylhexanoic acid and the 3-mercapto alcohol compound specifically increase by incubating the perspiration of the person having the apocrine odor (FIGS. 6 and 7).

(4) As the β-hydroxycarboxylic acid compound has not only a carboxyl group but also a hydroxyl group at the 3-position, a chemical modification can be performed in order to have good detection sensitivity in instrumental analyses such as a gas chromatography, a liquid chromatography or the like or to utilize the coloration reaction for assessing by a spectrometer or naked eye. Also, the β-hydroxycarboxylic acid and/or the derivative thereof can be separated from other substances which are low in contribution to the apocrine odor utilizing differences in polarity, solubility or the like.

(5) As the 3-mercapto alcohol compound has not only a hydroxyl group but also a mercapto group at the 3-position, a chemical modification can be performed in order to have good detection sensitivity in instrumental analyses such as a gas chromatography, a liquid chromatography or the like or to utilize the coloration reaction for assessing by a spectrometer or naked eye. Also, the 3-mercapto alcohol compound and/or the derivative thereof can be separated from other substances which are low in contribution to the apocrine odor utilizing differences in polarity, solubility or the like.

(6) As the β-hydroxycarboxylic acid compound and the 3-mercapto alcohol compound can be isolated by the adsorption chromatography or the like, the color reaction, which is sure, prompt and easy, can be utilized to evaluate quantitatively.

(7) Also, there are a spicy cumin-like odor and a fishy sulfur-like odor as major bad odors which comprise the apocrine odor. 3-Hydroxy-3-methylhexanoic acid is detected relatively in abundance from a person who has the strong spicy cumin-like odor. The 3-mercapto alcohol compound is detected relatively in abundance from a person who has the fishy sulfur-like odor.

Moreover, the β-hydroxycarboxylic acid compound, which is a group of compounds having a chemical structure quite similar to 3-hydroxy-3-methylhexanoic acid, is similar in characteristics such as chemical characteristics or organoleptic characteristics (particularly, odor) to 3-hydroxy-3-methylhexanoic acid, thus, the β-hydroxycarboxylic acid compound can be used as an objective index for assessing apocrine odor similarly to 3-hydroxy-3-methylhexanoic acid.

Therefore, by measuring the presence amount and the presence state of the β-hydroxycarboxylic acid and/or the derivative thereof (for instance, salt or ester of 3-hydroxy-3-methylhexanoic acid) in axillary regions by an appropriate means which is chemical, physical or the like, the apocrine odor in the axillary regions can be measured objectively and quantitatively with the use of the β-hydroxycarboxylic acid compound and/or the derivative thereof as an index.

Also, by measuring the presence amount and the presence state of the 3-mercapto alcohol compound and/or the derivative thereof (for instance, salt or ester of 3-mercapto-3-methylhexanol) in axillary regions by an appropriate means which is chemical, physical or the like, the apocrine odor in the axillary regions can be measured objectively and quantitatively with the use of the 3-mercapto alcohol compound and/or the derivative thereof as an index.

Particularly in the present invention, by using the β-hydroxycarboxylic acid compound and/or the derivative thereof and the 3-mercapto alcohol compound and/or the derivative thereof in combination, both cumin-like apocrine odor and sulfur-like apocrine odor can be evaluated, thus, an accurate evaluation can be performed in accordance with an actual apocrine odor. Also, in the case of using such a combination for the assessment of body odor and effectiveness of a deodorant, the level of body odor of a human or axillary odor, which is a part of body odor, can be assessed objectively and quantitatively not only from presence and strength of apocrine odor in the axillary regions but also from difference in quality thereof so that the accuracy of the assessment result can be raised.

The β-hydroxycarboxylic acid compound of the substance (A) is a group of compounds including 3-hydroxy-3-methylhexanoic acid and compounds having a chemical structure quite similar thereto, which have an odor quite similar to the apocrine odor and is represented by the following formula (1). 3-Hydroxy-3-methylhexanoic acid is represented by the following formula (3):

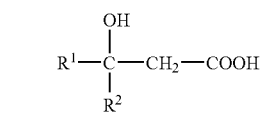

Formula (1)

wherein $R^1$ is an alkyl having 1 to 4 carbons; $R^2$ is a hydrogen atom or an alkyl having 1 to 4 carbons, and the total number of carbons in the formula (1) is 10 or less;

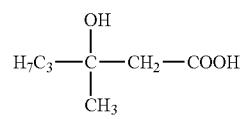

Formula (3)

In the above formula (1), $R^1$ is an alkyl having 1 to 4 carbons, which may be a straight or branched alkyl. For example, there may be methyl, ethyl, n-propyl, i-propyl, n-butyl, i-butyl and t-butyl. It can be considered that the β-hydroxycarboxylic acid compound is easier to use as an indicator material if the characteristic is closer to 3-hydroxy-3-methylhexanoic acid. Hence, in order to have the chemical structure close to 3-hydroxy-3-methylhexanoic acid, it is preferable that $R^1$ has 3 or 4 carbons, particularly the case of 3 carbons is preferable, and is preferably a straight-chain alkyl.

In the above formula (1), $R^2$ is a hydrogen atom or an alkyl having 1 to 4 carbons, which may be a straight or branched alkyl. As $R^2$, for example, there may be methyl, ethyl, n-propyl, i-propyl, n-butyl, i-butyl and t-butyl. In order to have the chemical structure of the β-hydroxycarboxylic acid compound close to 3-hydroxy-β-methylhexanoic acid, it is preferable that $R^2$ has 1 or 2 carbons, particularly the case of 1 carbon is preferable.

Among the β-hydroxycarboxylic acid, 3-hydroxy-3-methylhexanoic acid, 3-hydroxy-3-methylpentanoic acid, 3-hydroxy-3-methylbutanoic acid, 3-hydroxyhexanoic acid and 3-hydroxypentanoic acid are preferable. Among the above, 3-hydroxy-3-methylhexanoic acid is particularly suitable as an indicator material since 3-hydroxy-3-methylhexanoic acid itself is a major causative substance of apocrine odor present in the perspiration of the axillary regions as aforementioned.

3-Mercapto alcohol compound of the substance (C) in the present invention is contained relatively in large quantity in the perspiration of a person having the apocrine odor, and it is a group of compounds including 3-mercapto-3-methylhexanol, 3-mercaptohexanol, 3-mercaptopentanol, 3-mercapto-2-methylpentanol, 3-mercapto-2-methylbutanol and compounds having a chemical structure quite similar to those compounds, which has odor quite similar to the apocrine odor and is represented by the following formula (2). 3-Mercapto-3-methylhexanol, 3-mercaptohexanol, 3-mercaptopentanol, 3-mercapto-2-methylbutanol and 3-mercapto-2-methylpentanol are represented by the following formulae (4a) to (4e).

Formula (2)

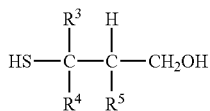

wherein $R^3$ is a hydrogen atom or methyl group; $R^4$ is an alkyl group having 1 to 3 carbons; and $R^5$ is a hydrogen atom or a methyl group, the total number of carbons in the formula (2) is 8 or less.

Formula (4a):

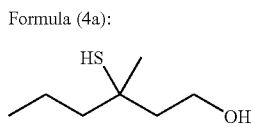

3-mercapto-3-methylhexanol

Formula (4b):

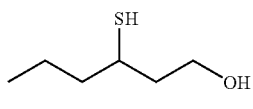

3-mercaptohexanol

Formula (4c):

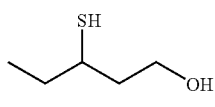

3-mercaptopentanol

Formula (4d):

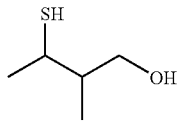

3-mercapto-2-methylbutanol

Formula (4e):

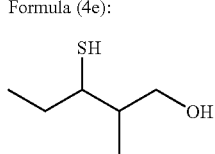

3-mercapto-2-methylpentanol

It can be considered that the 3-mercapto alcohol compound is easier to use as an indicator material if the characteristic is closer to 3-mercapto-3-methylhexanol which is contained in the perspiration in relatively large quantity among those compounds. Hence, it is preferable to have the chemical structure close to 3-mercapto-3-methylhexanol.

From the viewpoint, $R^3$ in the above formula (2) is preferably methyl group among hydrogen atom and methyl group. $R^4$ is an alkyl group having 1 to 3 carbons, which may be a straight or branched alkyl, and examples of which include methyl, ethyl, n-propyl and i-propyl. Particularly, it is preferable that $R^4$ has 2 or 3 carbons, and more preferably 3 carbons. Also, $R^5$ may be a hydrogen atom or a methyl group. Among them, a hydrogen atom is preferable.

Among the 3-mercapto alcohol compounds, 3-mercapto-3-methylhexanol, 3-mercaptohexanol, 3-mercaptopentanol, 3-mercapto-2-methylpentanol and 3-mercapto-2-methylbutanol are preferable. Among them, 3-mercapto-3-methylhexanol is particularly suitable for an indicator material since 3-mercapto-3-methylhexanol is contained in the perspiration of the axillary regions relatively in large quantity.

The substance (A) of the present invention may be subject to chemical modification so as to be used as the substance (B) in order to be detected in high sensitivity in the gas chromatography or liquid chromatography or be assessed by a spectrometer or naked eye utilizing the coloring reaction unless it does not lose the detection function as an indicator material. For example, an atom(s) or an atomic group(s) may be introduced to one or both of a carboxyl group and/or a hydroxyl group in the β-position of the β-hydroxycarboxylic acid compound and then used as derivatives such as salt, ester, amide, ether or the like.

As a reagent which can be used in the liquid chromatography analysis, spectrophotometer analysis or colorimetry test, and reacts with a carboxyl group of the β-hydroxycarboxylic acid compound, there may be the reagents which can lead to acid hydrazide such as 2-nitrophenylhydrazine, 6,7-dimethoxy-1-methyl-2(1H)-quinoxaline-3-propionyl carboxylic acid hydrazide (DMEQ-H), p-(4,5-diphenyl-1H-imidazole-2-il)-benzohydrazide, p-(1-methyl-1H-phenanthro-[9,10-d]imidazole-2-il)-benzo hydrazide, p-(5,6-dimethoxy-2-benzothiazoyl)-benzohydrazide or the like; the reagents which can lead to ester such as 9-anthryldiazomethane, 1-naphthyldiazomethane, 1(2naphtyl)diazoethane, 1-pyrenyldiazomethane, 4-diazomethyl-7-methoxycoumarin, 4-bromomethyl-7-methoxycoumarin (Br-MmC), 3-bromomethyl-6,7-dimethoxy-1-methyl-2(1H)-quinoxalinone, 9-bromomethylacridine, 4-bromomethyl-6,7-methylenedioxycoumarin, N-(9-acridinyl)-bromoacetamide, 2-(2,3-naphthylimino)ethyltrifluoromethane sulfonate, 2-(phthalimino)ethyltrifluoromethane sulfonate, N-chloromethylphthalimide, N-chloromethyl-4-nitrophthalimide, N-chloromethylisatin, o-(p-nitrobenzyl)-N,N'-diisopropylisourea (PNBDI) or the like; the reagents which can lead to amide such as monodansylcadaverine, 2-(p-aminomethylphenyl)-N,N-dimethyl-2H-benzotriazole-5-amine or the like.

As a reagent which can be used in the liquid chromatography analysis, spectrophotometer analysis and colorimetry test, and reacts with a hydroxyl group of the β-hydroxycarboxylic acid compound, there may be the reagents such as cerium ammonium nitrate in order to lead to a coordination compound, the reagents such as 4-(2-phthalimidyl)benzoyl chloride and the derivative thereof in order to lead to ester, the reagents such as 4-diazomethyl-7-methoxycoumarin in order to lead to ester, or the like.

Also, the β-hydroxycarboxylic acid compound may be led to inorganic salt, hydroxamic acid, acid chloride, a copper complex, cobalt complex or the like, and then further led to a chromophiric compound. The inorganic salt of the β-hydroxycarboxylic acid compound may be led to a chromophiric ester, the hydroxamic acid may be led to a chromophiric metal salt, acid chloride may be led to a chromophiric amide, and a copper complex or a cobalt complex of hydroxycarboxylic acid may be led to a chromophiric chelate compound respectively.

As a reagent which leads the inorganic salt of the β-hydroxycarboxylic acid compound to a chromophiric ester, there may be p-nitro benzyl bromide, phenacyl bromide, p-chlorophenacyl bromide, p-bromophenacyl bromide (PBPB), p-iodophenacyl bromide, p-nitrophenacyl bromide, p-phenylphenacyl bromide, p-phenylazophenacyl bromide, N,N-dimethyl-p-aminobenzeneazophenacyl chloride or the like. As a reagent which leads the hydroxamic acid to a chromophiric complex salt, there may be ferric chloride, vanadium or the like. As a reagent which leads the acid chloride to a chromophiric amide, there may be 9-aminophenanthrene or the like. As a reagent which leads the copper complex or cobalt complex of a hydroxycarboxylic acid compound to a chromophiric chelate compound, there may be diethyldithiocarbamate, bis(cyclohexanone)oxalyldihydrazone, vasocupreine or the like. They may be used by optional choice as required.

As a reagent which can be used in the gas chromatography analysis, and reacts with a carboxyl group and/or a hydroxyl group of the β-hydroxycarboxylic acid compound, there may be a silylation reagent such as N-trimethylsilylimidazole (TMSI), N,O-bis(trimethylsilyl) acetamide (BSA) or the like, an acylation reagent such as trifluoroacetic anhydride, trifluoroacetylimidazole or the like.

The component (C) of the present invention may be subject to chemical modification so as to be used as a substance (D) in order to be detected in high sensitivity in the gas chromatography or liquid chromatography or to be assessed by a spectrophotometer or naked eye utilizing the coloring reaction unless it does not lose a detection function as an indicator material. For example, an atom(s) or atomic group (S) may be introduced to one or both of a mercapto group and/or a hydroxyl group atom at the 3-position of a 3-mercapto alcohol compound and then used as derivatives such as salt, ether, ester or the like.

As a reagent and method which and can be used in the liquid chromatography analysis, spectrophotometer analysis and colorimetry test and can be used for reacting with the mercapto group of a 3-mercapto alcohol compound, there may be a fluorescence method which uses N-(9-acridinyl)maleimide (NAM), 4-chloro-7-sulfobenzofurazane ammonium salt (SBDCl), 4-fluoro-7-sulfobenzofurazane ammonium salt (SBD-F), 4-fluoro-7-sulfamoylbenzofrazane (ABD-F), N-[4-(5,6-methylenedioxy-2-benzofuranyl)phenyl]maleimide (MBPM), N-[4-(6-dimethylamino-2-benzofuranyl)phenyl]maleimide (DBPM), N-[p-(2-benzimidazolyl)phenyl]maleimide, monobromobiman, 5,5-dithiobis (2-nitrobenzoic acid), phenanzine methosulfate, o-phthal aldehyde, together with 2-aminoethanol, which may be used by optional choice as required.

As a reagent which can be used in the liquid chromatography analysis, spectrophotometer analysis or colorimetry test and can be used for reacting with a hydroxyl group of a 3-mercapto alcohol compound, there may be 3-chlorocarbonyl-6,7-dimethoxy-1-methyl-2(1H)-quinoxalinone (DMEQ-COCL), 2-(5-chlorocarbonyl-2-oxazoyl)-5,6-methylenedioxybenzofuran, 3,4-dihydro-6,7-dimethoxy-4-methyl-3-oxoquinoxaline-2-carbony 1 chloride, phthalimidylbenzoyl chloride, 1-anthroylnitrile, 9-anthroylnitrile, 7-methoxycoumarin-3-carbonylazide, p-phenylazobenzoyl chloride, 4-dialkylamino-3,5-dinitrobenzoyl chloride, p-nitrobenzoyl chloride, 3,5-dinitrobenzoyl chloride or the like.

As a reagent which can be used in the gas chromatography analysis and can be used for reacting with a mercapto group and/or hydroxyl group of a 3-mercapto alcohol compound, there may be a silylation reagent such as hexamethyldisilazane (HMDS), N-trimethylsilil imidazole or the like, an acylation reagent such as trifluoroacetic anhydride, trifluoroacetylimidazole or the like.

In the case of using a compound in which having a chromophore of a visible region is introduced as a labeled compound of the β-hydroxycarboxylic acid compound and/or the 3-mercapto alcohol compound, the level of apocrine odor can be assessed visually by comparing the concentration-color standard sample which has been preliminary prepared in relation to the concentration of the labeled compound with coloration generated from perspiration of a human using the same reagent.

The β-hydroxycarboxylic acid compound and the derivative thereof are suitable for the indicator material in terms of capability in objective evaluation and assessment of the apocrine odor at any time and anywhere since they can be synthesized and the synthesized product with a certain quality can be stably supplied. The β-hydroxycarboxylic acid compound can be synthesized, for example, according to the following formula (5), wherein ester having a hydroxyl group at the β-position is synthesized by the Reformatsky Reaction disclosed in Reformatsky Reaction: Ber. 20, 1210 (1887) and J. Russ. Phys. Chem. Soc., 22, 44 (1890), and the ester is hydrolyzed.

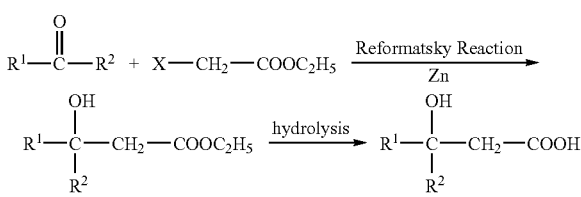

Formula (5)

wherein $R^1$ and $R^2$ are the same as aforementioned, and "X" is a halogen atom.

Also, the 3-mercapto alcohol compound and the derivative thereof are suitable for the indicator material in terms of capability in objective evaluation and assessment of the apocrine odor at any time and anywhere since they can be synthesized and the synthesized product with a certain quality can be stably supplied.

The 3-mercapto alcohol compound can be synthesized, for example, according to the formula (6). That is, the 3-mercapto alcohol compound is synthesized by preparing a derivative (a) of fatty ester having unsaturated structure at the β-position, introducing benzylmercaptan or the like as a thio ether group to the 3-position of the carbonyl carbon of the derivative (a) to obtain a derivative (b) by the addition reaction, reducing the derivative (b) with the use of a reducing agent such as lithium aluminum hydride or the like to convert the ester group to an alcohol group to obtain a derivative (c), and continuously leading the thio ether group to a mercapto group by the Birch reduction.

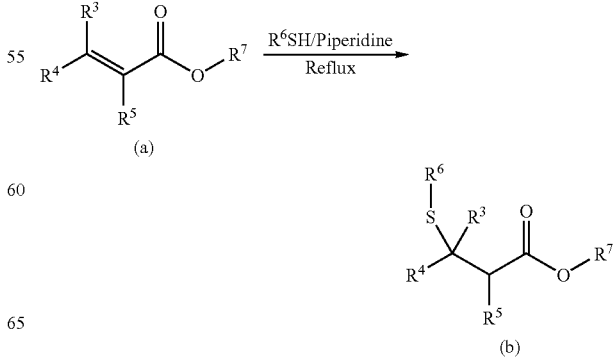

Formula (6)

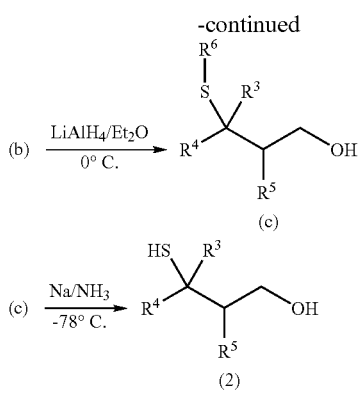

wherein $R^3$, $R^4$ and $R^5$ are the same as the formula (2), $R^6$ is a benzyl group and $R^7$ is an alkyl group.

The synthesized β-hydroxycarboxylic acid compound and 3-mercapto alcohol compound may be converted as required to the salt, ester or the other derivative by known means.

The β-hydroxycarboxylic acid compound and 3-mercapto alcohol compound, which have an asymmetric carbon atom, may be synthesized as a racemic mixture, or each enantiomer may be separately formed by asymmetric synthesis. Also, the racemic mixture may be subjected to the optical resolution and thereafter it may be used.

In the indicator material for assessing body odor of the present invention, certainly the substance (A) and/or the substance (C) itself can be used as an indicator component, derivatives of the above mentioned indicator substances such as the substance (B) and/or the substance (D) also may be used. Also, not derived substance and a derived substance may be used in a combination. For example, combinations of: the substances (A) and (D); the substances (C) and (B); and the substances (A), (C) and (D) may be used as an indicator material. Also, one or more kinds from each group of substances (A) to (D) may be used in combination. Further, one or more kinds may be selected from known causative agents of the body odor of apocrine odor, acid odor or the like such as acetic acid, butyric acid, isovaleric acid, 3-methyl-2-hexenoic acid, 4-ethylheptanoic acid, 7-octenoic acid, 1-octene-3-one, cis-1,5-octadiene-3-one, 3α-androstenol, 3α-androstenon to be added to the indicator material for assessing body odor of the present invention.

According to the indicator material for assessing body odor of the present invention, it is possible to prepare an indicator material which corresponds to various odors of the apocrine odor different in feeling between cumin-like and sulfur-like by changing weight ratio of the substance (A) and the substance (C) if necessary. Particularly, from the view point of having the presence ratio similar to the perspiration in the actual axillary regions, it is preferable that the weight ratio in terms of "the substance (C): the substance (A)" is 1:10 to 1:1,000 (weight ratio), more preferably 1:10 to 1:500, and most preferably 1:50 to 1:200.

In the present invention, a body odor can be assessed with the use of an indicator material of the present invention.

That is, in order to access the level of body odor of a human or axillary odor which is a part of the body odor objectively and quantitatively in terms of presence or strength of apocrine odor of the axillary regions, the synthesized β-hydroxycarboxylic acid compound and/or the derivative thereof can be used to determine quantity and observe the content of the β-hydroxycarboxylic acid compound and/or the derivative thereof contained in the perspiration of the axillary regions.

Also, the synthesized 3-mercapto alcohol compound and/or the derivative thereof can be used to determine quantity and observe the content of the 3-mercapto alcohol compound and/or the derivative thereof contained in the perspiration of the axillary regions. Further, the synthesized β-hydroxycarboxylic acid compound and/or the derivative thereof and the synthesized 3-mercapto alcohol compound and/or the derivative thereof can be used to determine quantity and observe the content of the β-hydroxycarboxylic acid compound and/or the derivative thereof and the 3-mercapto alcohol compound and/or the derivative thereof contained in the perspiration of the axillary regions.

Each of the selected indicator material may be solely used as an indicator material or may be used as an indicator material containing plural substance in mixture in the process of assessment steps.

Also, in the present invention, body odor can be assessed by using one or more kinds of β-hydroxycarboxylic acid compound and the derivative thereof and/or one or more kinds of 3-mercapto alcohol compound and the derivative thereof as an index. That is, "using as an index" in the present invention means to measure and evaluate the substances (A), (B), (C) and/or (D) contained in the perspiration. Typically, it means the case of using an indicator material preliminarily prepared by synthesis or the like, however, it may be a method which does not use an indicator material. For example, it may be a method to measure the substances (A), (B), (C) and/or (D) contained in the perspiration in a certain method and evaluate the level of body odor or effectiveness of a deodorant based on a standard data such as a calibration curve or the like obtained preliminarily.

In order to measure the presence amount and the presence state of the β-hydroxycarboxylic acid compound and/or the 3-mercapto alcohol compound or the derivative thereof of the present invention, there may be adapted some methods to obtain perspiration originated from a human, such as a method that test subjects is made to enter a room under the high temperature environment and subjected to thermal sweating and then perspiration of the axillary regions is collected in a test tube or the like, a method that a cotton pad is attached to the axillary regions for a certain time, a method that perspiration in the axillary regions is wiped off by a cotton wool or the like.

The 3-mercapto alcohol compound is produced 10 to 100 times or more by incubating the perspiration originated from a human having the apocrine odor under the anaerobic atmosphere. On the other hand, it is not produced even by incubating the perspiration originated from a human who does not have an apocrine odor.

Utilizing this feature, analysis after incubation of the obtained perspiration makes it easier to detect the 3-mercapto alcohol compound, usefulness of the substance (C) as indicator material enhances, and accuracy of the assessment result can be enhanced at the same time. Further, by utilizing this feature, the 3-mercapto alcohol compound may be industrially produced as an indicator material.

Also, if an apocrine sweat is secreting in the axillary regions but the perspiration is not decomposed by microorganism and the odor is not exhibited, it means that there is a latent state of the apocrine odor. In such a state, an accurate evaluation cannot be performed even if an organoleptic test or a research on the relationship with an axillary odor is conducted.

On the contrary, by assessing body odor using an indicator material of the present invention after incubating perspiration originated from a human under an anaerobic atmosphere, it is possible to evaluate if a test subject has a constitution which may produce an apocrine odor, that is, it is possible to conduct a potential evaluation.

As a method to prepare an anaerobic or microaerophilic atmosphere for producing the 3-mercapto alcohol compound in large quantity from perspiration collected, it is not particularly limited as far as the method can remove oxygen in the incubation atmosphere and replace with carbon dioxide. There may be methods such as filling with mixed gas (nitrogen and carbon dioxide) artificially prepared, using an agent which generates carbon dioxide by vacuuming up oxygen gas or the like. Also, instead of the binary mixed gas (nitrogen and carbon dioxide), a triple mixed gas (nitrogen, carbon dioxide and hydrogen) may be used. As a method of reducing concentration of remaining oxygen, there may be a method wherein the remaining oxygen is absorbed by a reduction steel wool, and a method which converts the oxygen into water using catalyst.

The concentration of oxygen gas under an anaerobic or microaerophilic atmosphere may be in the range of 0 to 10 v/v % (volume in volume percent, hereinafter may be simply referred as "%"), preferably 0 to 5%, more preferably 0 to 1%. Also, the concentration of carbon dioxide may be in the range of 5.0 to 22.0%, preferably 10.0 to 22.0%, more preferably 20.0 to 22.0%.

The incubation temperature of perspiration originated from a human for producing the 3-mercapto alcohol compound in large quantity may be in the range of 15 to 45° C., preferably 20 to 40° C., more preferably 25 to 38° C. Also, the incubation time of perspiration may be in the range of 6 to 336 hours, preferably 12 to 240 hours, more preferably 24 to 168 hours.

As a method for assessing body odor of the present invention using an indicator material for assessing body odor of the present invention or using one or more kinds among the substances (A), (B), (C) and (D) as an index, there may be a direct organoleptic test by human olfaction and a quantitative evaluation based on the chemical analysis, which may be used by adapting to various known evaluation systems.

In the case of conducting an organoleptic test by olfaction, an indicator material of the present invention in which 3-hydroxyl-3-methyl hexanoic acid or the derivative thereof and/or the 3-mercapto alcohol compound or the derivative thereof is diluted in several degrees to prepare odor standard samples of each concentration. Then, odor of test sample prepared using the perspiration collected from axillary regions and the standard samples are matched to assess the amount of 3-hydroxyl-3-methyl hexanoic acid and/or the 3-mercapto alcohol compound contained in the perspiration by the organoleptic test.

In the case of measuring content of the substance (A) and the substance (C) contained in the perspiration of the axillary regions by GC-MS, 3-hydroxyl-3-methyl hexanoic acid or the derivative thereof and the 3-mercapto alcohol compound or the derivative thereof are preferably used as a standard material (standard) to form each calibration curve. Using the calibration curve, a peak of 3-hydroxyl-3-methyl hexanoic and the 3-mercapto alcohol compound is respectively identified, and the amount is measured.

In the case of using such an instrumental analysis, an indicator material containing the substance (B) and the substance (D) which are respectively derivatives obtained by reacting the substance (A) and the substance (C) with the labeled material, fluorescent reagent or the like which is easily detectable may be used. Also, As a method for detecting the substance (C) and/or the substance (D) which is the derivative thereof, there is a method to introduce an extract of the obtained perspiration of a human as a specimen using an organic solvent or the like directly to the gas chromatography furnished with the highly sensitive sulfur detector.

Also, as a measuring method for assessing body odor, a coloration reagent may be added to the substance (A) and/or the substance (C) separated from the perspiration so as to measure the exhibited color by the spectrometer or conduct a colorimetry assessment with the naked eye.

In the case of utilizing the coloration reaction, a visual organoleptic test can be performed by preliminarily preparing coloration standard samples of various concentration in a form of colometric tubes filled with an aqueous solution or a form of test papers impregnating labeled compound with the use of an indicator material containing the substance (A) and the substance (C) reacted with a coloration reagent or the like, and comparing the changed color obtained by reacting the collected perspiration with the coloration reagent with the coloration standard samples.

In this way, the level of body odor or axillary odor, which is a part of the body odor, can be assessed by quantitatively evaluating strength of the odor due to the substance (A) and strength of the odor due to the substance (C) with the use of odor or parameter other than odor and then assessing comprehensively.

Also, if there is a production amount of 3-hydroxy-1-3-methyl hexanoic acid and/or the 3-mercapto alcohol compound is in large quantity in the axillary regions but they are changed to a derivative thereof which has no odor or weak odor such as a salt or the like, it means that there is a latent state of the apocrine odor. In such a state, an accurate evaluation cannot be performed even if an organoleptic test or a research on the relationship with an axillary odor is conducted. On the contrary, since derivatives having latent odor of 3-hydroxyl-3-methyl hexanoic acid and/or and the 3-mercapto alcohol compound can be analyzed and converted to the quantity of the substance (A) and the substance (C) according to the present invention, it is possible to evaluate if a test subject has a constitution which may produce axillary odor, that is, it is possible to conduct a potential evaluation.

An indicator material of the present invention can be utilized for the chemical analysis, the instrumental analysis, the organoleptic test or the like as described above and is capable of quantitative assessment with high objectivity. Particularly, by expressing the measured value as the quantity of the β-hydroxycarboxylic acid compound and/or the derivative thereof and the 3-mercapto alcohol compound and/or the derivative thereof with the use of the chemical analysis, instrumental analysis or the like, the subjectivity can be excluded from the assessment result and body odor can be assessed objectively and quantitatively.

Further in the present invention, the effectiveness of a deodorant targeting the apocrine odor can be assessed objectively and quantitatively with the use of an indicator material of the present invention or the substances constituting such a indicator material as the index.

As a method for assessing effectiveness of a deodorant, the indicator material may be used as a simple substance but also may be used as a composition prepared by compounding other substances, for example, a solvent for dissolution or dilution, or an additive such as stabilizer, deodorant, bactericide, antibacterial agent, surfactant, antioxidant, perfume, plant extracts or the like so as to be adapted to the practical usage such as preservation, use in assessment test or the like.

The deodorant targeting the apocrine odor may be of any kinds of function mechanism such as a kind which prevents decomposition of perspiration by disinfecting bacteria on the skin, a kind which decomposes or changes an odor substance to an odorless derivative, a kind which masks out odor or the like. A method for using the β-hydroxycarboxylic acid compound and/or the derivative thereof, the 3-mercapto alcohol compound and/or the derivative thereof, or both of them in combination as an indicator material for assessing effectiveness of a deodorant may not be particularly limited and may be used according to the function mechanism of a deodorant and the evaluation system.

For example, the effectiveness of a deodorant sample can be assessed objectively and quantitatively by adding a predetermined amount of the deodorant sample to an indicator material containing the β-hydroxycarboxylic acid compound and/or the derivative thereof, preferably 3-hydroxy-3-methylhexanoic acid or the derivative thereof, and the 3-mercapto alcohol compound or the derivative thereof, preferably 3-mercapto-3-methylhexanol, 3-mercaptohexanol, 3-mercaptopentanol, 3-mercapto-2-methylpentanol, 3-mercapto-2-methylbutanol or the derivatives thereof in a predetermined concentration as the indicator substance, and quantitatively determining the changed state of the indicator material in an appropriate method.

As a method for quantitatively determining the changed state of the indicator material, if the deodorant sample is a kind which decomposes or leads the β-hydroxycarboxylic acid and/or the 3-mercapto alcohol compound to other compound to reduce odor, an instrumental analysis may be performed using a calibration curve of the indicator material which is preliminarily formed or a chemical analysis may be performed such as the titration or extraction of a changed product or an unchanged state of the indicator material to determine quantity. If the deodorant sample is a kind which masks out the apocrine odor, the masking effect may be assessed by the organoleptic test wherein the indicator material is diluted to several levels to prepare odor standard samples of each concentration and the odor of indicator material which is added with the deodorant sample is matched to the standard samples.

Also, the quantitatively measurement may be conducted using a labeled compound of the β-hydroxycarboxylic acid and/or the 3-mercapto alcohol compound such as a fluorescent labeled compound, in such manner that a predetermined amount of the deodorant sample is added to an indicator material containing such a labeled compound in a predetermined concentration and then the instrumental analysis is performed for determining the changed state of the indicator material with the use of the calibration curve of the same indicator material. Also, a labeled portion of the labeled compound to detect when a predetermined amount of deodorant sample is added to an indicator material containing a labeled compound in a predetermined concentration and thereafter the quantity of a changed product or an unchanged state of the indicator material is determined by the chemical analysis such as the titration, extraction or the like.

Further, it is also possible to apply a deodorant sample actually on the axillary regions of a human to evaluate and compare each perspiration of the axillary regions obtained before and after the application with the use of an indicator material of the present invention.

In this way, effectiveness of a deodorant can be objectively and quantitatively assessed by quantitatively evaluating the strength of odor due to the substance (A) and the strength of odor due to the substance (C) contained in the apocrine odor of an indicator material of the present invention in which a deodorant is effected with the use of odor or parameter other than odor and then assessing comprehensively.

As aforementioned, the level of body odor of a human or axillary odor, which is a part of the body odor, can be objectively and quantitatively assessed from the viewpoint of presence, strength and difference in quality of the apocrine odor in the axillary regions by using an indicator material for assessing body odor containing at least one member selected from the group consisting of the β-hydroxycarboxylic acid compound represented by the formula (1) (substance (A)), the derivative of the substance (A) (substance (B)), the alcohol compound having a mercapto group at the 3-position represented by the formula (2) (substance (C)) and the derivative of the substance (C) (substance (D)), or using at least one member selected from the group consisting of the above-mentioned substances (A), (B), (C) and (D) as an index.

Particularly, the odor due to the substance (A) and the odor due to the substance (C) can be comprehensively evaluated by using an indicator material for assessing body odor containing at least one member selected from the group consisting of the substance (A) and/or the substance (B) and at least one member selected from the group consisting of the substance (C) and/or the substance (D), or by using the substance (A) and/or (B) and the substance (C) and/or (D) in combination as an index. Therefore, the apocrine odor which humans actually smell can be more accurately assessed.

An indicator material for assessing body odor of the present invention can objectively and quantitatively assess the body odor particularly by expressing measured value as content of the substance (A) and/or (B) or the substance (C) and/or (D) through the chemical analysis, instrumental analysis or the like.

Even if the perspiration in the axillary regions is changed to derivatives having no odor or weak odor such as the salt, ester or the like of β-hydroxycarboxylic acid compound and/or the salt, ester or the like of 3-mercapto alcohol compound, the β-hydroxycarboxylic acid compound and/or the 3-mercapto alcohol compound in a sample can be detected or quantitated by an indicator material of the present invention. Therefore, the latent state of axillary odor, namely, the state without odor or with weak odor can be also objectively and accurately evaluated.

Also, if an apocrine sweat is secreting in the axillary regions but the perspiration is not decomposed by microorganism and the odor is not generated, it means that there is a latent state of the apocrine odor. Even in such case, it is possible to evaluate if a test subject has a constitution which may produce an apocrine odor, that is, it is possible to conduct a potential evaluation by incubating perspiration originated from a human according to the present invention.

Further, in the present invention, an assessment result can be accurately obtained corresponding to deodorizing and masking effect against apocrine odor of a deodorant using an indicator material containing a substance selected from the substances (A) and (B) and/or a substance selected from the substances (C) and (D), or using a substance selected from the substances (A) and (B) and/or a substance selected from the substances (C) and (D) as an index. Therefore, the effectiveness of a deodorant targeting apocrine odor can be objectively and quantitatively assessed.

In the present invention, it is also possible to produce an indicator material of the present invention by utilizing the characteristic that the content of 3-mercapto alcohol compound increases by the incubation of perspiration in the axillary regions of a person having apocrine odor.

A kit for assessing body odor of the present invention is a product which is a combination of at least a coloration reagent which reacts with β-hydroxycarboxylic acid originated from perspiration of a human and accessories assisting a reaction of the β-hydroxycarboxylic acid and/or other substances causing body odor originated from perspiration with the coloration reagent and an assessment based on the coloration. In the accessories for assistance, there are essential accessories such as extraction means used for pretreatment which is always performed prior to the coloration reaction or assessment, and accessories which improves convenience such as facilitation, simplification or the like of the coloration reaction or assessment.

A kit for assessing body odor includes, for example, equipments and reagents for extracting or separating the β-hydroxycarboxylic acid and/or fatty acid having 12 or less carbons other than said β-hydroxycarboxylic acid from the perspiration in the axillary regions, and one or more reagents which exhibits color by reacting with the β-hydroxycarboxylic acid and/or fatty acid having 12 or less carbons other than said β-hydroxycarboxylic acid originated from perspiration of a human. Further, the kit may include 3-hydroxy-3-methylhexanoic acid as an indicator substance.

Figure 8:
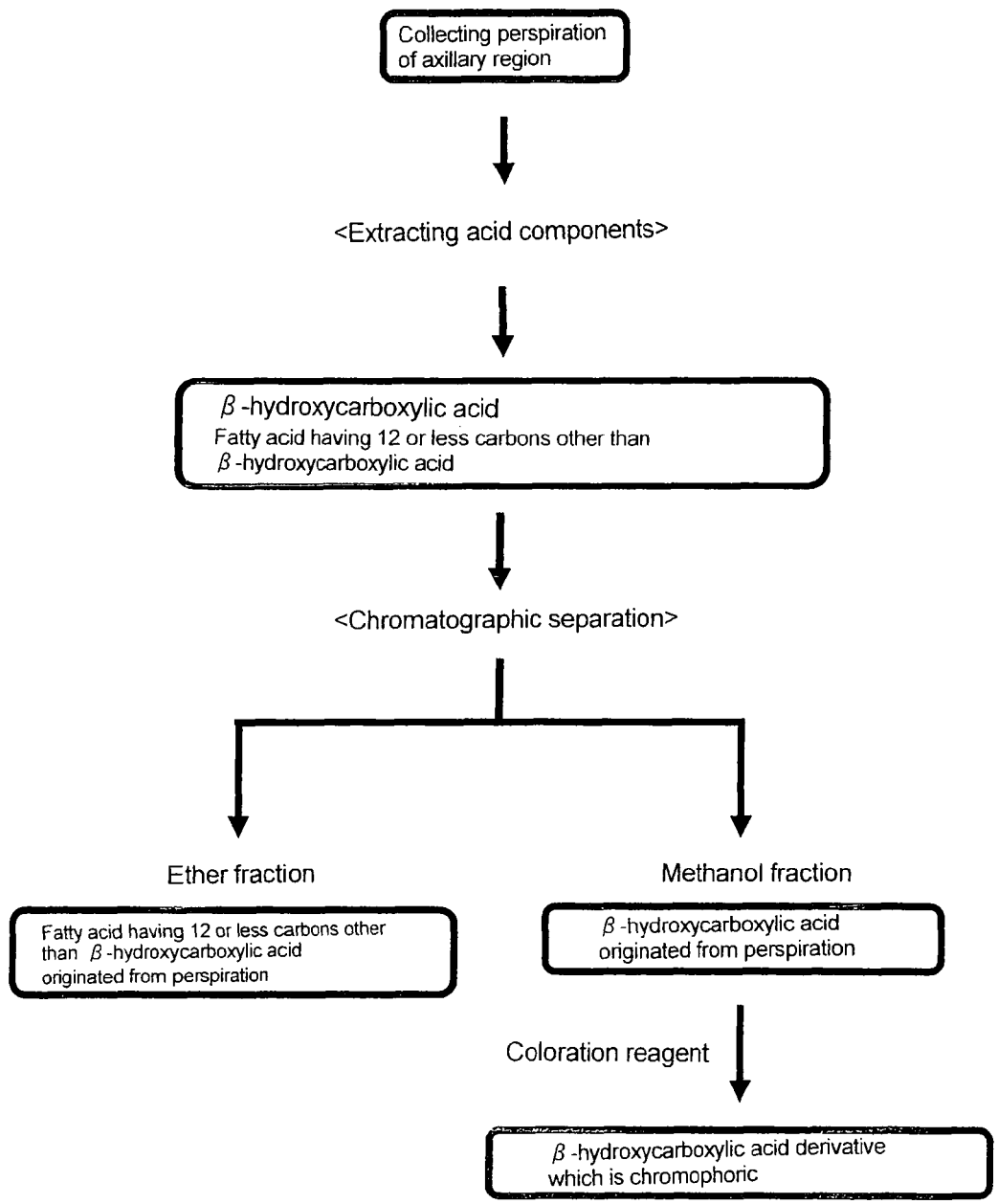
FIG. 8 shows the process of assessing the level of body odor.
Figure 9:
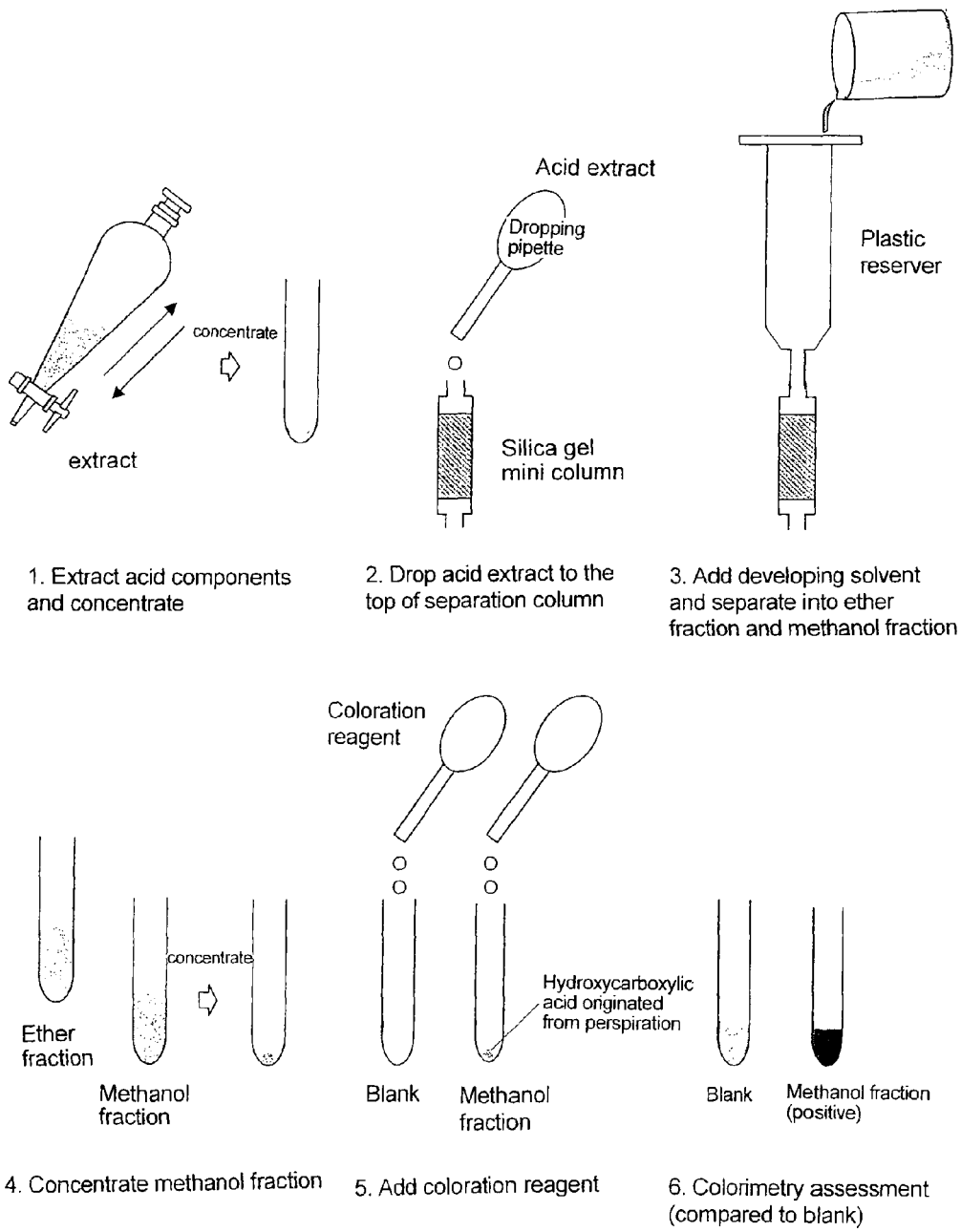
FIG. 9 shows the method of using a kit for assessing the level of body odor with the use of an absorption column chromatography.
Figure 10:
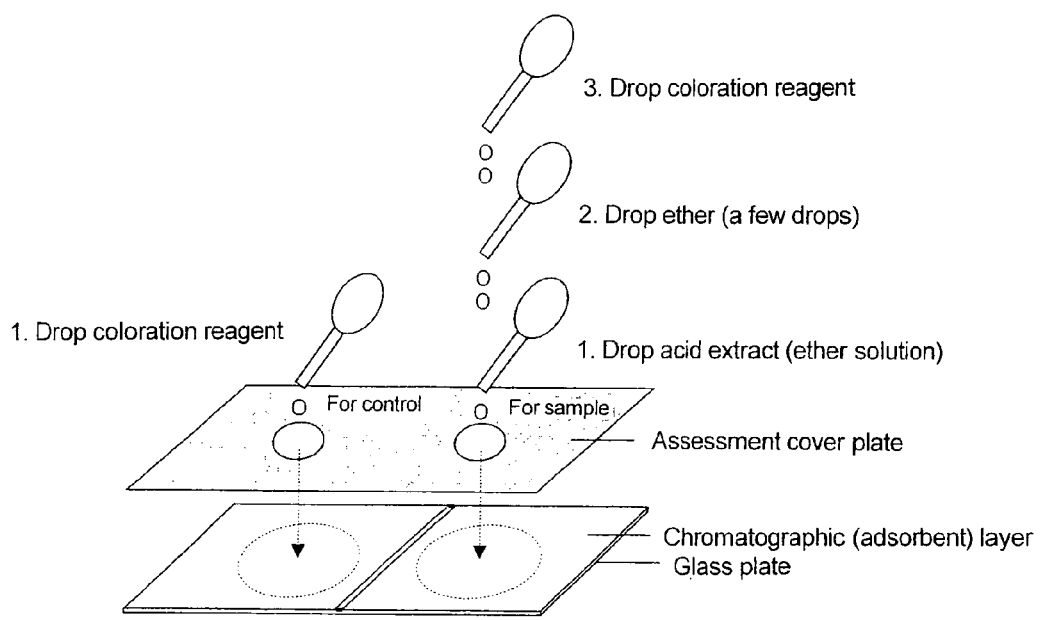
FIG. 10 shows the method of using a kit for assessing the level of body odor with the use of a thin-layer column chromatography.
Figure 10:
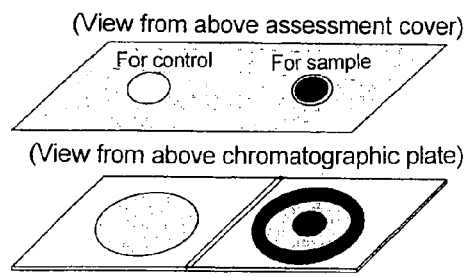
Figure 10:
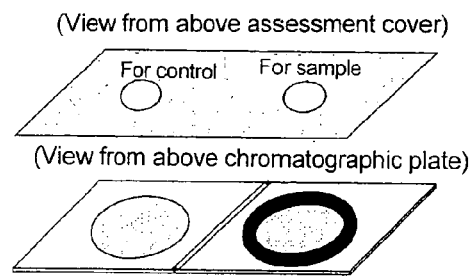

FIG. 8 shows a schematic diagram of a process of assessing body odor originated from perspiration of a human, particularly apocrine odor, utilizing the coloration reaction of the β-hydroxycarboxylic acid and fatty acid having 12 or less carbons other than said β-hydroxycarboxylic acid. Also, FIGS. 9 and 10 show typical equipment included in the kit for assessing body odor and examples of the utility thereof.

As a method of collecting perspiration of the axillary regions, there may be the method which directly collects perspiration generated by the thermal sweating in test tubes or the like, the method wherein test subjects wear T-shirt with cotton pads sawn at a position corresponding to underarm for a certain time, or the method which directly wipes perspiration in the underarm with gauze or the like.

As a method of extracting the acid material contained in the perspiration, it is not limited as far as the method can extract the acid material. Generally, the acid-base extraction by alkali aqueous solution is used. As the alkaline aqueous solution, there may be sodiumhydrodencarbonate aqueous solution, sodium carbonate aqueous solution, sodium hydroxide aqueous solution, potassium hydroxide aqueous solution or the like. It is also possible to extract the acid material by using the ion-exchange resin.

As a method to assess a level of the apocrine odor, there may be the method wherein the acid material extracted in the above process is separated into β-hydroxycarboxylic acid and fatty acid having 12 or less carbons other than said β-hydroxycarboxylic acid respectively, and thereafter a coloration reagent is added to the separated β-hydroxycarboxylic acid to observe an exhibited color.

A method to separate β-hydroxy carboxylic acid and the fatty acid having 12 or less carbons other than said β-hydroxycarboxylic acid in the acid material is not particularly limited as far as the method can separate using polarity of molecule. There may be utilized the absorption chromatography wherein a glass tube or plastic tube is filled with an appropriate adsorbent such as silica gel powder or the like, the thin-layer chromatography wherein a glass or plastic plate or the like is coated with an appropriate adsorbent such as silica gel or the like.

The absorption column chromatography can discharge in ascending order of adsorbability to take up separately as components having high adsorbability stays in the upper part and components having lower adsorbability run off faster when the solution of the above acid material is flowed off from the top of the glass tube. In the case of using the acid material originated from perspiration of a human as a sample, for example, as shown in FIG. 9, after eluting fatty acid having 12 or less carbons other than said β-hydroxycarboxylic acid with the use of a middle polar solvent such as diethyl ether, β-hydroxycarboxylic acid can be taken up with the use of a high polar solvent such as methanol. Hence, when a coloration reagent is added to a methanol fraction and the methanol fraction to generate coloration, the presence of the β-hydroxycarboxylic acid can be confirmed. Also, the hue of test solution can be quantified by measurement using equipments such as a spectrophotometer or color-difference meter as well as the organoleptic test by the naked eye.

The thin-layer chromatography is the method which separates molecules different in polarity on a plate, for example as shown in FIG. 10, if the acid material originated from the perspiration of a human is dropped in the predetermined position of a plate and then developed with the use of the middle polar solvent such as diethyl ether, the fatty acid having 12 or less carbons other than said β-hydroxycarboxylic acid spreads around together with the solvent, however, β-hydroxycarboxylic acid stays in the dropped position. Hence, if a coloration reagent is dropped in the center of the dropped spot to generate coloration, the presence of β-hydroxycarboxylic acid originated from perspiration can be confirmed. In this manner, the thin-layer chromatography method can directly spray the coloration reagent on the plate, therefore, the qualitative or quantitative coloration test can be performed quickly.

As a method which assess presence or quantity of β-hydroxycarboxylic acid using the coloration reaction, there may be: (1) a method which directly introduces a chromophore to a hydroxyl group or a carboxyl group of β-hydroxycarboxylic acid; (2) a method which converts β-hydroxycarboxylic acid to the derivative thereof and introduces a chromophore to the derivative; (3) a method which decomposes β-hydroxycarboxylic acid and introduces a chromophore to the decomposed product; or the like.

(1) As a coloration reagent which is used in a method which directly introduces a chromophore to a hydroxyl group or a carboxyl group of β-hydroxycarboxylic acid and reacts with a carboxyl group of β-hydroxycarboxylic acid to exhibit color, there may be a reagent which leads the β-hydroxycarboxylic acid to a chromophiric acid hydrazide in the presence of a condensing agent to generate coloration, a reagent which leads the β-hydroxycarboxylic acid to a chromophiric ester to generate coloration, a reagent which leads the β-hydroxycarboxylic acid to a chromophiric amide to generate coloration or the like.

As a coloration reagent which leads β-hydroxycarboxylic acid to the chromophiric acid hydrazide, there may be 2-nitrophenylhydrazine, 6,7-dimethoxy-1-methyl-2(1H)-quinoxaline-3-propionyl carboxylic acid hydrazide (DMEQ-H), p-(4,5-diphenyl-1H-imidazole-2-yl)-benzohydrazide, p-(1-methyl-1H-phenanthro-[9,10-d]imidazole-2-yl)-benzo hydrazide, p-(5,6-dimethoxy-2-benzothiazoyl)-benzohydrazide or the like.

As a reagent which leads β-hydroxycarboxylic acid to the chromophiric ester to generate coloration, there may be 9-anthryldiazomethane, 1-naphthyldiazomethane, 1-(2-naphthyl) diazomethane, 1-pyrenyldiazomethane, 4-diazomethyl-7-methoxycoumarin, 4-bromomethyl-7-methoxycoumarin, 3-bromomethyl-6,7-dimethoxy-1-methyl-2(1H)-quinoxalinone, 9-bromomethylacridine, 4-buromomethyl-6,7-methylenedioxycoumarin, N-(9-acridinyl)-bromoacetamide, 2-(2,3-naphthylimino)ethyltrifluoromethane sulfonate, 2-(phthalimino)ethyltrifluoromethane sulfonate, N-chloromethylphthalic imide, N-chloromethyl-4-nitrophthalic imide, N-chloromethylisatin, o-(p-nitrobenzyl)-N,N'-diisopropylisourea or the like.

As a reagent which leads the β-hydroxycarboxylic acid to the chromophiric amide to generate coloration, there may be monodansylcadaverine, 2-(p-aminomethylphenyl)-N,N-dimethyl-2H-benzotriazole-5-amine or the like.

As a coloration reagent which reacts with a hydroxyl group of β-hydroxycarboxylic acid to generate coloration, there may be a reagent which leads to a chromophiric coordination compound to generate coloration, a reagent which leads to a chromophiric ester to generate coloration, a reagent which leads to a chromophiric ether to generate coloration or the like. As a reagent which leads to the chromophiric coordination compound to generate coloration, there may be cerium nitrate ammonium or the like. As a reagent which leads to the chromophiric ester to generate coloration, there may be 4-(2-phthalimidyl)benzoyl chloride, the isomer there of, the derivative there of or the like. As a reagent which leads to the chromophiric ether to generate coloration, there may be 4-diazomethyl-7-methoxycoumarin or the like.

(2) As a derivative of β-hydroxycarboxylic acid which can be utilized for the coloration reaction in the method which converts β-hydroxycarboxylic acid to the derivative thereof and then introduces a chromophore to the derivative, there may be inorganic salt, hydroxamic acid, acid chloride, copper complex, cobalt complex or the like.

The inorganic salt of β-hydroxycarboxylic acid reacts with aromatic halogen to be led to the chromophiric ester, hydroxamic acid is led to the chromophiric metal salt, acid chloride is led to the chromophiric amide, a copper complex and a cobalt complex of the hydroxycarboxylic acid are led to a chelate compound which react with copper and cobalt respectively to generate coloration.

As a method to convert β-hydroxycarboxylic acid to inorganic salt, there may be a method which mixes the β-hydroxycarboxylic acid with the alkaline material such as sodium hydrogen carbonate solution, sodium carbonate solution, sodium hydroxide solution, potassium hydroxide solution or the like to neutralize. As an aromatic halogen which reacts with inorganic salt of the hydroxycarboxylic acid to be led to the chromophiric ester, there may be p-nitrobenzyl bromide, phenacyl bromide, p-chlorophenacyl bromide, p-bromophenacyl bromide, p-iodinephenacyl bromide, p-nitrophenacyl bromide, p-phenylphenacyl bromide, p-phenylazophenacyl bromide, N,N-dimethyl-p-aminobenzeneazophenacyl chloride or the like.

As a method to convert β-hydroxy carboxylic acid to hydroxamic acid, there may be a method which reacts β-hydroxy carboxylic acid with hydroxylamine in the presence of a condensing agent, a method which reacts β-hydroxy carboxylic acid with hydroxylamine hydrochloride using nickel as catalyst or the like. As a metal reagent which forms the chromophiric complex salt with hydroxamic acid, there may be ferric chloride, vanadium or the like.

As a method to convert β-hydroxycarboxylic acid to acid chloride, there may be a method which reacts β-hydroxycarboxylic acid with oxalylchloride or the like. As a method to lead acid chloride to the chromophiric amide, there may be a method which reacts it with 9-aminophenanthrene in the presence of triethylamine or the like.

As a reagent which forms the chromophiric chelate compound (complex) with copper or cobalt, there may be diethyldithiocarbamic acid, bicyclohexanoneoxalyldihydrazone, bathocuproin or the like.

(3) As a method which decomposes β-hydroxycarboxylic acid and makes the decomposed product exhibit color, there may be a method wherein acyl-CoA synthetase is effected to β-hydroxycarboxylic acid in the presence of adenosine triphosphoric acid (ATP) and coenzyme CoA to produce acyl-CoA, which is then processed with acyl-CoA oxidase to produce enoyl-CoA and hydrogen peroxide, the hydrogen peroxide is further processed with catalase to obtain formaldehyde, and the obtained formaldehyde is reacted with 4-amino-3-hydrazino-5-mercapto-1,2,3-triazole (AHMT), which is a coloration reagent, to exhibit purple color which is used for the colorimetry test.

In this manner, the reagent used for the coloration reaction of β-hydroxycarboxylic acid in the present invention may not be particularly limited as far as the reagent reacts with β-hydroxycarboxylic acid, the derivative of β-hydroxycarboxylic acid or the decomposed product of β-hydroxycarboxylic acid. A compound having a hydrazino group such as 2-nitrophenylhydrazine (2-NPH) or the like, which has high sensitivity in detecting β-hydroxycarboxylic acid originated from the perspiration of a human and is easy to perform the colorimetry test with the naked eye, or a compound having a diazomethyl group such as 9-anthryldiazomethane (ADAM) or the like, which has high sensitivity in detecting and reacts under a mild condition, are suitably used.

The coloration reaction using 2-nitrophenylhydrazine is a reaction (Formula (7)) in which β-hydroxycarboxylic acid reacts with 2-nitrophenylhydrazine in water or alcohol solution in the presence of a condensing agent to produce acid hydrazide which exhibits magenta under the alkali condition:

Formula (7)

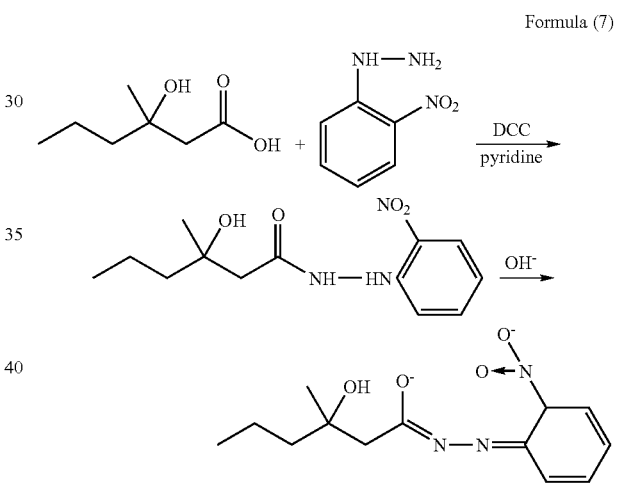

As a condensing agent, there may be utilized, dicyclohexylcarbodiimide (DCC), 1-ethyl-3-(3-dimethylaminopropyl)carbodiimide (EDC) orthelike. As an alkaline agent, there may be utilized potassium hydroxide solution or the like.

When 0.5 mL of water or alcohol solution containing 0.02M 2-nitrophenylhydrazine hydrochloride is added to 0.5 mL of water or alcohol solution containing 0.01 to 0.05 μM 3-hydroxy-3-methylhexanoic acid, the test solution exhibits slightly brownish yellow. Also, when 0.5 mL of water or alcohol solution containing 0.02M 2-nitrophenylhydrazine is added to 0.5 mL of water or alcohol solution containing 0.05 to 1 μM 3-hydroxy-3-methylhexanoic acid, the test solution exhibits sienna to dark magenta. On the contrary, when water or alcohol solution containing 2-nitrophenylhydrazine is added to water or alcohol solution not containing hydroxycarboxylic acid, acid hydrazide is not produced and the test solution remains yellow, which is an original color of unreacted 2-nitrophenylhydrazine.

As aforementioned, the strength of the apocrine odor is proportional to the content of β-hydroxycarboxylic acid in the perspiration. Hence, a level of apocrine odor can be surely, quickly and easily assessed by observing the developed color of a test solution with the naked eye.

The coloration reaction using 9-anthryldiazomethane is a method to lead β-hydroxycarboxylic acid to 9-anthrylmethyl ester having strong fluorescence (Formula (8)):

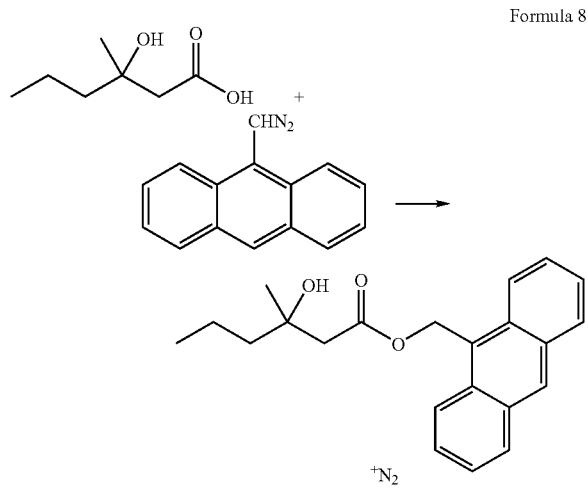

Formula 8

The reaction does not need a catalyst or heat and finishes in about 10 to 60 minutes at room temperature. 9-Anthrylmethyl ester in methanol has the excitation wavelength of 365 nm and the fluorescent wavelength of 412 nm.

When 1.0% 9-anthryldiazomethane in methanol or acetone solution is added to methanol solution containing 0.01 to 0.05 μM 3-hydroxy-3-methylhexanoic acid followed by radiation with light of 365 nm, the test solution exhibits slightly bluish white. Further, when 1.0% 9-anthryldiazomethane in methanol or acetone solution is added to methanol solution containing 0.05 to 1 μM 3-hydroxy-3-methylhexanoic acid followed by radiation with light of 365 nm, the test solution exhibits strong blue fluorescence. On the contrary, even though 1.0% 9-anthryldiazomethaneinmethanol alcohol solution is added to a solution not containing β-hydroxycarboxylic acid, an ester having strong fluorescence is not produced.

As aforementioned, the strength of the apocrine odor is proportional to the content of β-hydroxycarboxylic acid in the perspiration. Hence, a level of apocrine odor can be surely, quickly and easily assessed by observing the developed color of a test solution with the naked eye.

In the present invention, when β-hydroxycarboxylic acid contained in the perspiration is separated from the perspiration of the axillary regions and thereafter quantitative evaluation is performed using a coloration reagent, synthesized 3-hydroxy-3-methylhexanoic acid can be used as a standard material (standard).

That is, the amount of β-hydroxycarboxylic acid contained in the perspiration can be more accurately determined by using the exhibited color of 3-hydroxy-3-methylhexanoic acid which is synthesized and weighed and a coloration reagent as standard. At the same time, the amount of β-hydroxycarboxylic acid is proportional to the strength of the apocrine odor, thus, a level of the apocrine odor can be assessed accurately.

The standard material, 3-hydroxy-3-methylhexanoic acid, used thereinmay be diluted to proper concentration in a laboratory, however, it is convenient if the standard material is diluted in a solvent such as methanol, acetone or the like so as to facilitate to take up a suitable amount for comparison. Particularly, it is preferable to use a standard solution diluted to the degree of being able to measure off, such as a diluted solution of About 1 to 1,000 μg 3-hydroxy-3-methylhexanoic acid in 100 μL diluent.

As aforementioned, the β-hydroxycarboxylic acid compound and the derivative thereof such as 3-hydroxy-3-methylhexanoic acid or the like can be synthesized by utilizing the Reformatsky reaction.

Also, in the present invention, if the difference in color between samples to compare is subtle or when assessing a level of apocrine odor reduced after the use of a deodorant or an operation to remove apocrine glands, it is possible to exclude objectivity from the assessment result by quantifying hue of the test solution with the use of an analytical instrument.

The analytical instrument used therein is not particularly limited as far as the instrument can measure the degree of exhibited color of the test solution. There may be used a colorimeter, ultraviolet-visible spectrophotometer or the like for acid hydrazide produced by the coloration reaction using 2-nitrophenyl hydrazine. Also, a fluorospectrophotometer or the like may be utilized for 9-anthrylmethyl ester produced by the coloration reaction using 9-anthryldiazomethane.

Further in the present invention, not only a level of apocrine odor specifically generated to the axillary regions of a person having tragomaschalia habit but also a level of acid odor (perspiration odor) generated in the axillary regions of a person not depending on having tragomaschalia habit can be quickly and easily assessed.

As a method for assessing a level of contribution of apocrine odor and acid odor, there may be a method wherein after separating an acid material extracted from perspiration into β-hydroxycarboxylic acid, which causes apocrine odor, and fatty acid having 12 or less carbons other than said β-hydroxycarboxylic acid, a coloration reagent is added thereto respectively to observe the exhibited colors, or a method wherein a coloration reagent is added to the acid material extracted from perspiration and β-hydroxycarboxylic acid separated from the acid material respectively to observe the exhibited colors.

As a method for assessing a level of acid odor, a coloration reagent may be added to fatty acid having 12 or less carbons other than said β-hydroxycarboxylic acid, which causes acid odor. For example, as shown in FIG. 9, in the adsorption column chromatography, a level of contribution of apocrine odor and acid odor can be quickly and easily assessed by eluting acid component originated from perspiration, which is mainly fatty acid having 12 or less carbons other than said β-hydroxycarboxylic acid with the use of diethyl ether as a developing solvent, thereafter eluting β-hydroxycarboxylic acid with the use of methanol, and then adding a coloration reagent to the obtained ether fraction and methanol fraction respectively to observe the exhibited color.

Also, in the thin-layer chromatography, the acid material extracted from perspiration of a human is dropped on a plate for the thin-layer chromatography to which a coloration reagent is dropped to let a whole acid material exhibit color. The color exhibited by a whole acid material has a positive correlation with respect to the total amount of β-hydroxycarboxylic acid, which is a component causing the apocrine odor, and fatty acid having 12 or less carbons other than said β-hydroxycarboxylic acid, which is a component causing the acid odor.

On the other hand, after dropping the extracted acid material on a similar plate for the thin-layer chromatography prepared separately and separating β-hydroxycarboxylic acid and fatty acid other than said β-hydroxycarboxylic acid with the use of the developing solvent, the coloration reagent is dropped on the β-hydroxycarboxylic acid remained in the center of the dropped spot to exhibit color. The color exhibited on this plate has a positive correlation with respect to the amount of β-hydroxycarboxylic acid, which is a major component causing the apocrine odor. Thus, by observing both exhibited colors, a level of contribution of apocrine odor and acid odor can be assessed.

Therefore, it is possible to assess a level of contribution of apocrine odor and acid odor of each test subject quickly and easily with the use of a kit for assessing body odor of the present invention.

As a coloration reagent which reacts with carboxylic acid contained in perspiration to generate coloration, which may not particularly limited as far as the coloration reagent reacts with a carboxyl group of fatty acid having 12 or less carbons, which has major contribution to acid odor, there may be utilized the aforementioned coloration reagent which reacts with a carboxyl group of β-hydroxycarboxylic acid to generate coloration.

In order to assess the kind and strength of body odor accurately, i.e. for an accurate assessment of the degree of each contribution of apocrine odor and acid odor with respect to the acid material originated from perspiration, it is preferable that the reactivity of coloration reagent is highly specific to β-hydroxycarboxylic acid and fatty acid having 12 or less carbons other than said β-hydroxycarboxylic acid and the coloration reaction with respect to other acid material is weak.

As aforementioned, a kit for assessing body odor of the present invention can surely, quickly and easily assess the level of body odor or comprehensive axillary odor, which is a part of body odor, focusing on presence and strength of apocrine odor of the axillary regions and further taking the presence and strength of acid odor into account without using expensive analytical instruments such as the gas chromatography, liquid chromatography or the like. Therefore, the kit can be utilized when conducting diagnosis on a level of apocrine odor of a person who is concerned about own axillary odor, or assessing effectiveness of a deodorant, an operation to remove apocrine glands or the like at inspection institutes such as hospital (dermatology or the like), health center or the like.

In the case of assessing whether an effort to reduce body odor such as the use of a deodorant or an operation to remove apocrine glands is actually effective, for example, the quantity of β-hydroxycarboxylic acid and/or fatty acid having 12 or less carbons other than said β-hydroxycarboxylic acid in the perspiration before and after the use of a deodorant may be determined and evaluated using a kit for assessing body odor of the present invention to compare. For example, if the time of collecting each sample is different, the first collected perspiration sample may be stored in an appropriate place such as a refrigerator so that the sample does not cause chemical change and the assessment test may be performed at the same time. When the quantity of β-hydroxycarboxylic acid and fatty acid having 12 or less carbons other than said β-hydroxycarboxylic acid in the perspiration is determined and evaluated, if the colors of test solutions are quantified by an analytical instrument, comparison and evaluation can be performed accurately even though the time when the assessment test is performed is different.

Also, a kit for assessing body odor of the present invention can be utilized for evaluating effectiveness of a deodorant sample or screening people having tragomaschalia habit at development research of deodorants targeting apocrine odor.

As a method for assessing effectiveness of a deodorant targeting apocrine odor, for example, the effectiveness of a deodorant sample can be assessed precisely, rapidly and easily by adding predetermined amount of a deodorant sample to a sample containing β-hydroxycarboxylic acid of a predetermined concentration, and assessing the amount of β-hydroxycarboxylic acid, preferably the amount of 3-hydroxy-3-methylhexanoic acid, with the use of a kit for assessing body odor of the present invention.

It is also possible to apply a deodorant sample actually on the axillary regions of a human and evaluate β-hydroxycarboxylic acid, preferably the amount of 3-hydroxy-3-methylhexanoic acid, contained in perspiration of the axillary regions collected respectively before and after the application with the use of a kit for assessing body odor of the present invention to compare.

As example of the constitution of the aforementioned kit, for example, there may be the followings, but may not be limited thereto.

(1) A package including a cotton wool, plastic cup or the like for collecting perspiration of a human, preferably processed to be usable without modification, and wrapped with an outer package as required;

(2) A package including reagents, solvents and equipments such as an aqueous solution of an alkali, organic solvent, separating funnel or the like for extracting acid material from the perspiration of a human in combination with the above constituents;

(3) A package including equipments such as columns for the adsorption chromatography, plates for the thin-layer chromatography or the like to separate β-hydroxycarboxylic acid and fatty acid having 12 or less carbons other than said β-hydroxycarboxylic acid originated from perspiration of a human in combination with constituents of any of the above packages;

(4) A package including middle polar solvents used for eluting fatty acid having 12 or less carbons other than the β-hydroxycarboxylic acid from acid material in the adsorption chromatography or the thin-layer chromatography in combination with constituents of any of the above packages;

(5) A package including high polar solvents used for eluting β-hydroxycarboxylic acid from a column in the adsorption chromatography in combination with constituents of any of the above packages;

(6) A package including a coloration reagent which reacts with β-hydroxycarboxylic acid originated from perspiration of a human, preferably filled in a container in which the coloration reagent is prepared in the condition of composition or concentration which can be used without modification in combination with constituents of any of the above packages and wrapped with an outer package as required;

(7) A package including a coloration reagent which reacts with fatty acid having 12 or less carbons other than the β-hydroxycarboxylic acid, preferably filled in a container in which the coloration reagent is prepared in the condition of composition or concentration which can be used without modification in combination with constituents of any of the above packages and wrapped with an outer package as required;

(8) A package including a coloration reagents which react with β-hydroxycarboxylic acid and fatty acid having 12 or less carbons other than the β-hydroxycarboxylic acid originated from perspiration of a human, preferably filled in a container in which the coloration reagents are prepared in the condition of composition or concentration which can be used without modification in combination with constituents of any of the above packages and wrapped with an outer package as required;

(9) A package including auxiliary reagents used for preliminary preparations prior to the coloration reaction when the quantity of β-hydroxycarboxylic acid is determined and evaluated using a coloration reagent after the β-hydroxycarboxylic acid is separated from perspiration of the axillary regions, for example, a preliminary preparation to lead the β-hydroxycarboxylic acid to the derivative, in combination with constituents of any of the above packages;

(10) A package including equipments such as ultraviolet lamps used for confirming a level of coloration of a test solution when the quantity of β-hydroxycarboxylic acid is determined and evaluated using a coloration reagent after the β-hydroxycarboxylic acid is separated from perspiration of the axillary regions in combination with constituents of any of the above packages;

(11) A package including a diluted solution of 3-hydroxy-3-methylhexanoic acid or 3-hydroxy-3-methylhexanoic acid which are preferably synthesized products and used as standard material (standard) when the quantity of β-hydroxycarboxylic acid contained in perspiration is determined and evaluated using a coloration reagent after said β-hydroxycarboxylic acid is separated from perspiration of the axillary regions in combination with constituents of any of the above packages;

(12) A package including color sample sheets for assessing a level of coloration of test solutions when the quantity of β-hydroxycarboxylic acid contained in perspiration is determined and evaluated using a coloration reagent after the β-hydroxycarboxylic acid is separated from perspiration of the axillary regions in combination with constituents of any of the above packages;

(13) A package including means for dropping such as a pipette or the like which is easy to take up and drop a single dose of a coloration reagent in combination with constituents of any of the above packages; and

(14) A package including analytical instrument such as the colorimeter, spectrometer or the like used for quantifying a level of exhibited color of test solutions in combination with constituents of any of the above packages.

A kit for assessing body odor of the present invention can surely, quickly and easily assess the level of body odor or axillary odor, which is a part of body odor, focusing on presence and strength of apocrine odor of the axillary regions and further taking the presence and strength of acid odor into account, utilizing the coloration reaction of β-hydroxycarboxylic acid, which is peculiarly present in perspiration of a person having apocrine odor, and/or fatty acid having 12 or less carbons other than the β-hydroxycarboxylic acid, which is a material causing acid odor or the derivative thereof or the decomposed product thereof.

Also, a kit for assessing body odor and a method for assessing body odor of the present invention can exclude objectivity from the assessment result by quantifying hue exhibited as the result of the coloration reaction of the test solution with the use of an analytical instrument such as a colorimeter or the like.

Further, a kit for assessing body odor and a method for assessing body odor of the present invention can be utilized as a sure, quick and easy kit or method for assessing body odor when conducting diagnosis on a level of apocrine odor of a person who is concerned about own axillary odor, assessing effectiveness of an operation to remove apocrine glands or the like, assessing effectiveness of a deodorant sample targeting apocrine odor or the like at a hospital, health center, research institute or the like.

EXAMPLE

The following examples further describe and demonstrate embodiments of the present invention. The examples are given solely for the purpose of illustration and are not to be construed as limitations of the present invention.

Example A

1. Screening of Test Subjects

Each of 65 healthy Japanese males selected at random as test subjects wore a new white T-shirt made of cotton for 24 hours consecutively and the T-shirts were collected. An organoleptic test by 7 professional panel members was conducted on the axillary regions of the collected T-shirts concerning kinds and strength of axillary odor.

<The Points of Evaluation for Odor>
Acid odor: sour and putrefactive odor
Cumin-like apocrine odor: spicy, woody and animal-like odor
Sulfur-like apocrine odor: fishy and soy sauce and grapefruit-like odor <The Evaluation Criteria of for Strength of Odor>
0: Odorless
1: Slight odor
2: Weak odor
3: Easily perceptible odor
4: Strong odor
5: Very strong odor As a result, 28 people were recognized to have little axillary odor (the strength of odor of these people was 1 or less) (herein after referred as Group A), 21 people were recognized to have weak axillary odor (the highest strength of odor of these people was 2 or 3) (herein after referred as Group B), and 16 people were recognized to have strong axillary odor (the highest strength of odor of these people was 4 or 5) (herein after referred as Group C).

The evaluation result of the Group C, which was recognized to have strong axillary odor, is shown in Table 1. As shown in Table 1, the test subjects having apocrine odor can be classified into a group shifting to the cumin-like odor (Subject identification Nos. 1 to 3) and a group shifting to the sulfur-like odor (Subject identification Nos. 4 to 9).

TABLE 1

Organoleptic evaluation result of Group C

| Subject identification No. | Lower fatty acid odor | Apocrine odor | |
|---|---|---|---|
| | | Cumin-like odor | Sulfur-like odor |
| 1 | 3 | 5 | 4 |
| 2 | 3 | 5 | 3 |
| 3 | 2 | 5 | 4 |
| 4 | 4 | 4 | 5 |
| 5 | 4 | 4 | 5 |
| 6 | 3 | 3 | 5 |
| 7 | 3 | 3 | 4 |
| 8 | 2 | 3 | 4 |
| 9 | 3 | 3 | 4 |
| 10 | 4 | 2 | 2 |
| 11 | 4 | 2 | 1 |
| 12 | 4 | 2 | 1 |

TABLE 1-continued

Organoleptic evaluation result of Group C

| Subject identification No. | Organoleptic evaluation result | | |
|---|---|---|---|
| | Lower fatty acid odor | Apocrine odor | |
| | | Cumin-like odor | Sulfur-like odor |
| 13 | 4 | 1 | 2 |
| 14 | 5 | 0 | 0 |
| 15 | 4 | 0 | 0 |
| 16 | 4 | 0 | 0 |

2. Analysis of Component Corresponding to Cumin-Like Odor

The test subjects were 13 people who were recognized to have a cumin-like apocrine odor in the Group C (Subject identification Nos. 1 to 13). A cotton pad was sewn on a part of a T-shirt corresponding to the axillary regions. After the test subjects wore the T-shirts for 24 hours, the T-shirts were collected and the cotton pad of the axillary region was subject to extraction in diethyl ether. The extract was divided into an acid fraction, a neutral fraction and a basic fraction by an acid-base extraction method, and volatile components were analyzed with the used of a Gas Chromatography-Mass Spectrometer (GC-MS). Important components which generate typical odors of perspiration of an axillary region were specified by a sniffing Gas Chromatography (sniffing GC).

Figure 1:
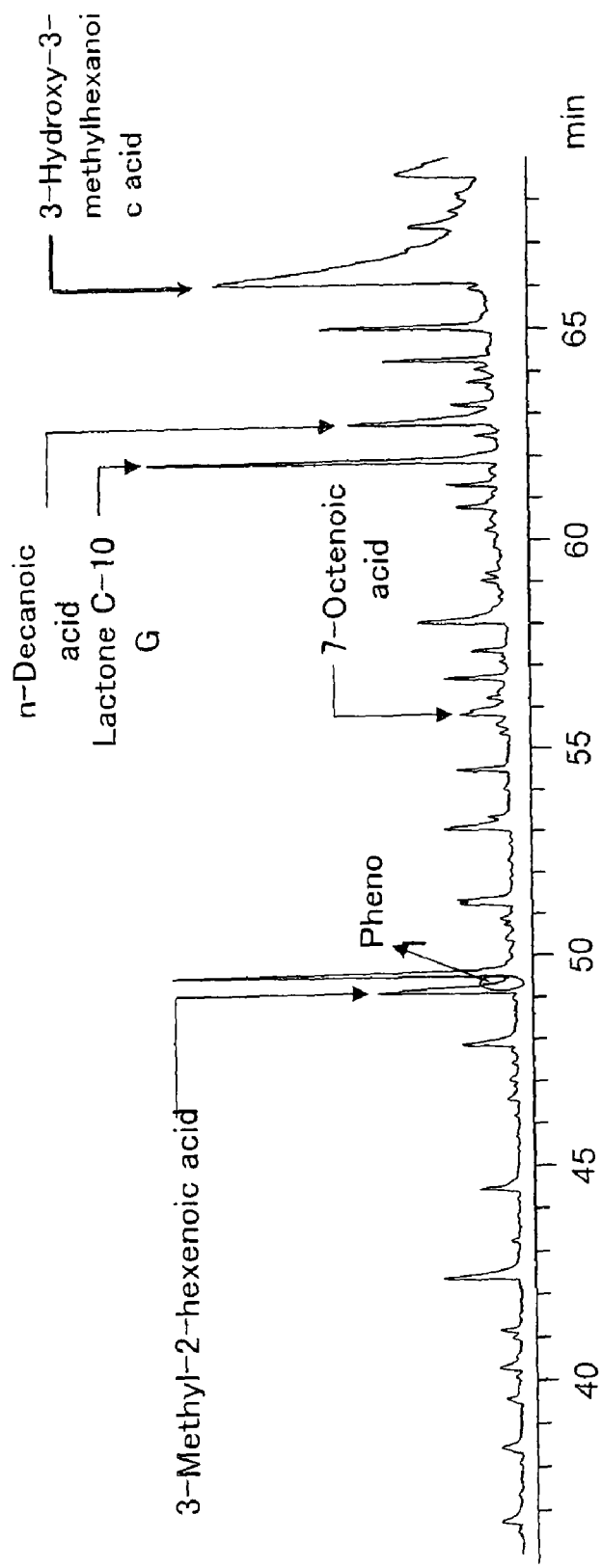
FIG. 1 shows the elution peaks as a result of GC-MS analysis of an acid extract of perspiration of a person having an apocrine odor.

<GC-MS Analysis Conditions>
Device: 6890GC-5973MSD (Agilent Technology)
Column: DB-WAX (60 m×0.25 mm×0.25 μm)
Temperature conditions: 40° C. (1 minute)→(6° C./min.)→60° C.→(2° C./min.)→300° C. (40 minutes)
Career gas: He
Ionization voltage: 70 eV By analyzing the acid extract, a new presence of 3-hydroxy-3-methylhexanoic acid was shown together with conventionally known presence of saturated fatty acid, 3-methyl-2-hexenoic acid, 7-octenoic acid and γ-lactones (FIG. 1). This component had a strong odor very similar to the apocrine odor at the time of performing the sniffing GC. Also, the amount of 3-hydroxy-3-methylhexanoic acid contained in the acid extract was calculated from a peak area and it was in the range of 0.1 to 64.3 μg. It was found that 3-hydroxy-3-methylhexanoic acid is present at high concentrations capable of being quantitatively detectable. 3-hydroxy-3-methylhexanoic acid has not reported as a constituent of an axillary odor of a human so far, however, 3-hydroxy-3-methylhexanoic acid was detected from all the test subjects.

Next, test subjects were 3 people who were recognized to have no apocrine odor in the Group C (Subject identification Nos. 14 to 16). A cotton pad was sewn on a part of a T-shirt corresponding to the axillary region. After the test subjects wore the T-shirts for 24 hours, the T-shirts were collected and the cotton pad of the axillary region was subject to extraction in diethyl ether. An acid fraction was extracted by an acid-base extraction method, and analyzed with the used of a Gas Chromatography-Mass Spectrometer (GC-MS).

Figure 2:
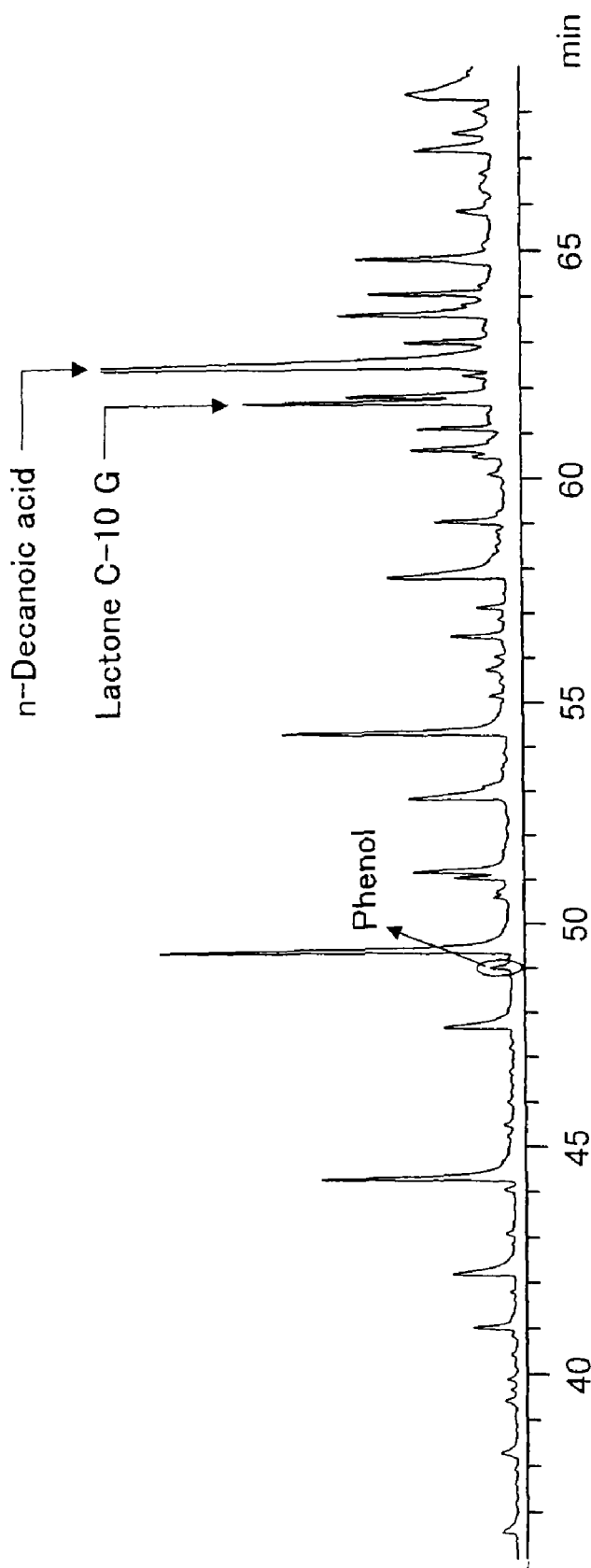
FIG. 2 shows the elution peaks as a result of GC-MS analysis of an acid extract of perspiration of a person having no apocrine odor.

As a result, as shown in FIG. 2, 3-hydroxy-3-methylhexanoic acid was not detected from any test subject.

3. Determining Quantity of 3-hydroxy-3-methylhexanoic Acid

Test subjects were 5 people who were recognized to have strong apocrine odors in the Group C (Subject identification Nos. 1 to 5), 4 people who were recognized to have weak apocrine odors in the Group C (Subject identification Nos. 10 to 13) and 3 people who were recognized to have no apocrine odor in the Group C (Subject identification Nos. 14 to 16). A cotton pad was sewn on a part of a T-shirt corresponding to the axillary region. After the test subjects wore the T-shirts for 24 hours, the T-shirts were collected and the cotton pad of the axillary region was subject to extraction in diethyl ether. An acid fraction was extracted by an acid-base extraction method. Then, a diluted solution using ether of the same volume was prepared by a 1 ml measuring flask (manufactured by DRAN). Using the diluted solution, the quantity of 3-hydroxy-3-methylhexanoic acid was determined with the use of a Gas Chromatography-Mass Spectrometer (GC-MS). A quantitative value was calculated from a peak area which was obtained by injecting 3-hydroxy-3-methylhexanoic acid having a given concentration to the GC-MS.

Figure 3:
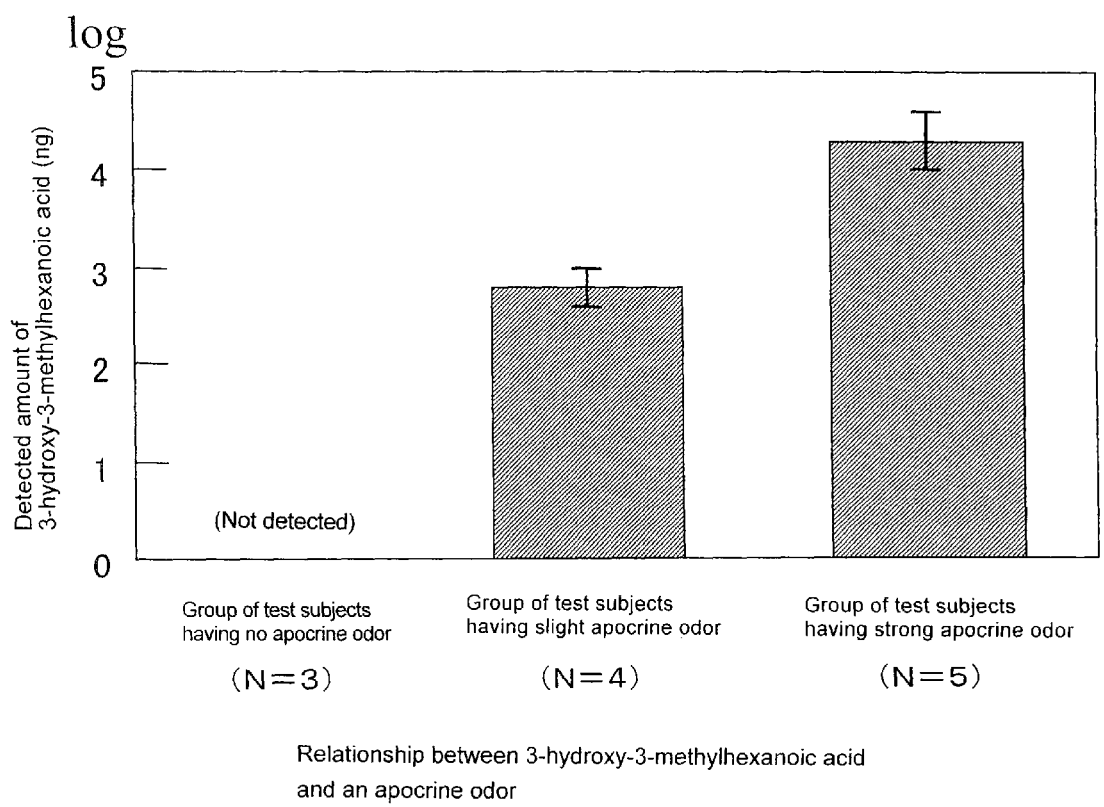
FIG. 3 is a graph showing the relationship between the amounts of 3-hydroxy-3-methylhexanoic acid contained in perspiration of axillary regions and the strength of an apocrine odor.

The relationship between the presence or level of apocrine odor and the detected amount of 3-hydroxy-3-methylhexanoic acid was obtained. As a result, as shown in FIG. 3, the amount of 3-hydroxy-3-methylhexanoic acid at the axillary region increased when the apocrine odor became stronger.

4. Analysis of Component Corresponding to Sulfur-Like Odor

The test subjects were 3 people who were recognized to have a sulfur-like apocrine odor in the Group C (Subject identification Nos. 4 to 6). About 1 mL of perspiration running from both axillary regions of each test subject was collected in a test tube in a room conditioned at 40° C. and 80% humidity. The test tube in which Twister (a stirrer coated with 100% polydimethylsiloxane, alias Stir Bar Sorptive Extraction; manufactured by Gerstel) was added was agitated for 30 minutes. Then, an analysis was performed with the use of a Gas Chromatography-Mass Spectrometer (GC-MS) equipped with a heat desorption device. Important components which generate typical odors of perspiration of an axillary region were specified by a sniffing Gas Chromatography (sniffing GC) equipped with a heat desorption device.

Figure 4:
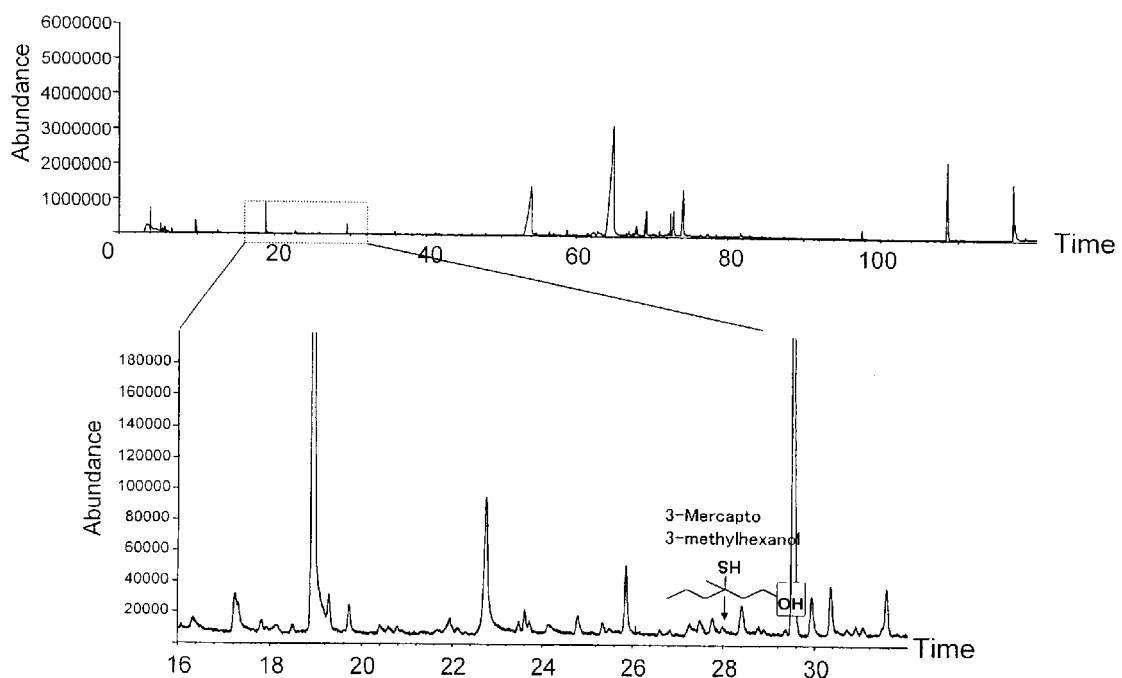
FIG. 4 shows the result of GC-MS analysis of the perspiration of a person having an apocrine odor.

<GC-MS Analysis Conditions>
Device: 6890GC-5973MSD (Agilent Technology)
Column: DB-1 (60 m×0.25 mm×0.25 μm)
Temperature conditions: 40° C. (1 minute)→(6° C./min.)→60° C.→(2° C./min.)→300° C. (40 minutes)
Career gas: He
Ionization voltage: 70 eV By analyzing the components of the apocrine odor contained in perspiration, a new presence of 3-mercapto-3-methylhexanol was shown by GC-MS analysis (FIG. 4). The eluted component had a strong odor very similar to the apocrine odor at the time of performing the sniffing GS. Also, the amount of 3-mercapto-3-methylhexanol was calculated from a peak area and it was in the range of 0.001 to 1.0 μg. It was found that the 3-mercapto-3-methylhexanol is present at high concentrations capable of being quantitatively detectable.

3-mercapto-3-methylhexanol has not reported as a constituent of an axillary odor of a human so far, however, 3-mercapto-3-methylhexanol was detected from all 3 test subjects.

Figure 5:
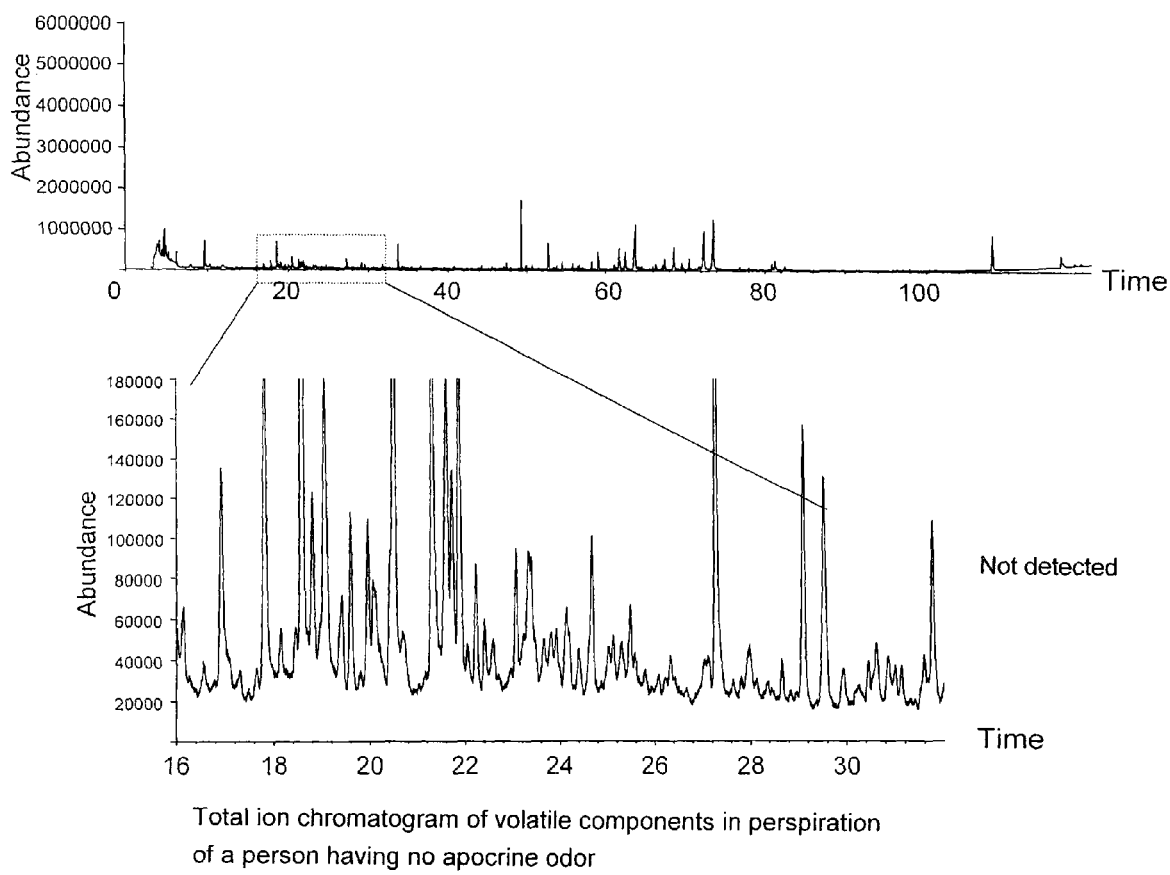
FIG. 5 shows the result of GC-MS analysis of the perspiration of a person not having apocrine odor.

Next, test subjects were 3 people who were recognized to have no apocrine odor in the Group C (Subject identification Nos. 14 to 16). About 1 mL of perspiration running from both axillary regions of each test subject was collected in a test tube in a room conditioned at 40° C. and 80% humidity. The test tube in which the Twister was added was agitated for 10 minutes. Then, an analysis was performed with the use of a Gas Chromatography-Mass Spectrometer (GC-MS) equipped with a heat desorption device. As a result, as shown in FIG. 5, 3-mercapto-3-methylhexanol was not detected from any test subject.

Test subjects were 3 people who were recognized to have a strong sulfur-like apocrine odor in the Group C (Subject identification Nos. 4 to 6) and 3 people who were recognized to have no apocrine odor in the Group C (Subject identification Nos. 14 to 16). About 1 mL of perspiration running from both axillary regions of each test subject was collected in a test tube in a room conditioned at 40° C. and 80% humidity. After the perspiration was incubated in an anaerobic environment (an oxygen concentration of 0.1% or less and a carbon dioxide concentration of 21%) at 30° C. for 48 hours, the test tube in which the Twister was added was agitated for 10 minutes. Then, an analysis was performed with the use of a Gas Chromatography-Mass Spectrometer (GC-MS) equipped with a heat desorption device. Important components which generate typical odors of perspiration of an axillary region were specified with the use of a sniffing Gas Chromatography (sniffing GC) equipped with a heat desorption device.

As a result, as shown in FIG. 6, 3-mercapto-3-methylhexanol, 3-mercaptohexanol, 3-mercaptopentanol, 3-mercapto-2-methylpentanol and 3-mercapto-2-methylbutanol were identified from the incubated perspiration of people having an apocrine odor. Each of these eluted components had a strong odor similar to the apocrine odor at the time of performing the sniffing GC, which became stronger by the incubation.

On the contrary, 3-mercapto-3-methylhexanol, 3-mercaptohexanol, 3-mercaptopentanol, 3-mercapto-2-methylpentanol and 3-mercapto-2-methylbutanol were not detected from the perspiration of any test subject having no apocrine odor even it was incubated (FIG. 7).

Example B

1. Preparation of an Indicator Material for Assessing Body Odor

Mixtures of 3-hydroxy-3-methylhexanoic acid (Substance (A)) and 3-mercapto-3-methylhexanol (Substance (C)) was prepared at a 0.015% diluted concentration in ethanol, wherein Substance (A):Substance (C)=50:1, 100:1 and 200:1, as indicator materials for assessing body odor for Example B-1, B-2 and B-3 respectively. Also, a 0.015% diluted solution of 3-methyl-2-hexenoic acid in ethanol was prepared as an indicator material for assessing body odor for Comparative Example B-2.

2. Evaluation of a Deodorizing and Masking Effect of an Indicator Material for Assessing Body Odor Against an Apocrine Odor The test subjects were 6 people in the Group A (who were recognized to have no axillary odor) of Example A. Each of the above-mentioned indicator materials for assessing body odor (Examples B-1 to B-3 in Table 2) was sprayed to an axillary region of each test subjects once (about 30 mg) to apply the indicator material for assessing body odor to the axillary regions of the test subjects having no apocrine odor. Then, after each of commercially available deodorant products A to E was sprayed to an axillary region of each test subject, to which the indicator material for assessing body odor was applied, for about 1 second, an organoleptic test by 10 professional panel members (5 males and 5 females) was conducted concerning a deodorant and masking effect of the deodorants.

Also, after each of the commercially available deodorant products A to E was sprayed to an axillary region of each of the test subjects who were recognized to have an apocrine odor (6 people who were recognized to have a strong apocrine odor in the Group C of Example A (Subject identification Nos. 1 to 6)) for about 1 second, an organoleptic test by 10 professional panel members (5 males and 5 females) was conducted concerning the deodorant and masking effect of the deodorants (Comparative example B-1).

The organoleptic test was conducted in a room maintained at 25° C. and 65% humidity. The evaluation was regarding 5 commercial products (commercially available deodorant products A to E shown in Table 2) in total so as to conducted one commercial product per day. An odor of the axillary region after treated with each commercial product evaluated according to the following criteria.

<The Evaluation Criteria for Odor>
0: Apocrine odor is not decreased
1: Apocrine odor is slightly decreased
2: Apocrine odor is decreased
3: Apocrine odor is significantly decreased The deodorant and masking effect of the commercially available deodorant products was assessed by using organoleptic test results of odor (average value) by 10 professional panel members, which was presented in the following 4 levels.

<The Criteria of Effectiveness Evaluation for Deodorants (Marks in Parentheses are Used in Table 2)>
0 or more and less than 0.5: Not effective (×)
0.5 or more and less than 1.5: Slightly effective (Δ)
1.5 or more and less than 2.5: Effective (◯)
2.5 or more and less than 3.0: Significantly effective (◎)

3. Results of Evaluation

Accuracy of the apocrine odor reproduced by the indicator material for assessing body odor is proved when the deodorant effect of the deodorants treated to the test subjects preliminarily treated by the indicator material for assessing body odor is considerably consistent with the deodorant effect of the deodorants treated to the test subjects having actual apocrine odors.

In Table 2, the deodorant effects of the deodorants treated to the test subjects preliminarily treated by the indicator material for assessing body odor of Comparative example B-2 and Examples B-1 to B-3 are compared based on the deodorant effect of the deodorants treated to the test subjects having actual apocrine odors (Comparative example B-1). As a result, Example B-2 was completely consistent with Comparative example B-1 and Examples B-1 and B-3 were mostly consistent with Comparative example B-1, which proved that the present invention as an indicator material can accurately reproduce the apocrine odor, and the deodorant and masking effect of a deodorant can be accurately assessed by the indicator material according to the present invention.

On the contrary, Comparative example B-2 was not consistent with Comparative B-1 at all, and Comparative example B-2 using 3-methyl-2-hexenoic acid could not assess the deodorant and masking effect of deodorants as a standard substance, which proved that Comparative example B-2 can not accurately reproduce the apocrine odor.

TABLE 2

Assessment results of effectiveness (deodorant and masking) of deodorants

| Deodorant product | Comparative Example B-1 Apocrine odor naturally generated from axillary | B-2 3-methyl-2-hexenoic acid | Example B-1 Mixture of 50:1 (Component A: Component C) | B-2 Mixture of 100:1 (Component A: Component C) | B-3 Mixture of 200:1 (Component A: Component C) |
|---|---|---|---|---|---|
| Commercial product A | Δ | X | Δ | Δ | Δ |
| Commercial product B | ◉ | Δ | ○ | ◉ | ◉ |
| Commercial product C | X | ○ | X | X | Δ |
| Commercial product D | Δ | X | Δ | Δ | ○ |
| Commercial product E | ○ | Δ | Δ | ○ | ○ |
| Consistency with Comparative example B-1 | — | Not consistent | Slightly consistent | Completely consistent | Slightly consistent |

Example C

1. Screening of Test Subjects

65 Healthy Japanese males cooperated as volunteers. Each of them wore a new white T-shirt made of cotton for 24 hours consecutively. After the T-shirts were collected, the strength of apocrine odor and acid odor was assessed by 7 professional panel members about axillary regions of T-shirts based on the following criteria.

<The Criteria of Organoleptic Test>
Intensity 0: Odorless
Intensity 1: Slight odor
Intensity 2: Weak odor
Intensity 3: Easily perceptible Odor
Intensity 4: Strong odor
Intensity 5: Very strong odor As a result, 10 people of test subjects were recognized to have apocrine odor of intensity 3 or more, 3 people were recognized to have apocrine odor of intensity 1 or 2, 52 people were recognized to have apocrine odor of intensity 0.

2. Quantification of 3-hydroxy-3-methyl Hexanoic Acid 4 people who were recognized to have apocrine odor of intensity 3 or more (Subject identification Nos. A to D), 3 people who were recognized to have apocrine odor of intensity 1 or 2 (Subject identification Nos. E to G), 3 people who were recognize to have no apocrine odor (intensity 0) (Subject identification Nos. H to J) were selected as test subjects.

A cotton pad was sewn on a part of a T-shirt corresponding to the axillary region of the sword arm. After the test subjects wore the T-shirts for 24 hours, the T-shirts were collected and the cotton pad of the axillary region was subject to the acid-base extraction to extract acid component originated from perspiration. Then, by using the silica gel mini column (Varian Bond Elute Jr), 10 mL of diethyl ether, and 10 mL of methanol, the acid extract was separated into a diethyl ether fraction and a methanol fraction. After concentrating the methanol fraction once, 1 mL of diluted solution was prepared by a measuring flask (manufactured by DURAN).

1 μL of the diluted solution was analyzed by the gas chromatography-mass spectrometer (GC-MS). Using a synthesized 3-hydroxy-3-methylhexanoic acid as a standard material (standard), an calibration curve was drawn, and the amount of 3-hydroxy-3-methylhexanoic acid contained in perspiration was measured.

The result of organoleptic test on axillary odor and quantification of 3-hydroxy-3-methylhexanoic acid is shown in FIG. 3. 3-Hydroxy-3-methylhexanoic acid was detected from the methanol fractions of all test subjects who were recognized to have apocrine odor (Subject identification Nos. A to G). On the contrary, 3-hydroxy-3-methylhexanoic acid was not detected from the diethyl ether fraction.

TABLE 3

| Subject identification No. | Organoleptic test Intensity of apocrine odor | Intensity of acid odor | Detected amount of 3-hydroxy-3-methyl-hexanoic acid (μg) Methanol fraction | Ether fraction |
|---|---|---|---|---|
| A | 4 | 4 | 33.93 | Not Detected |
| B | 5 | 5 | 64.29 | " |
| C | 3 | 3 | 15.71 | " |
| D | 4 | 4 | 37.5 | " |
| E | 2 | 2 | 1.71 | " |
| F | 1 | 2 | 0.87 | " |
| G | 2 | 2 | 1.39 | " |
| H | 0 | 1 | Not Detected | " |
| I | 0 | 2 | " | " |
| J | 0 | 1 | " | " |

<The Criteria of Organoleptic Test>
Intensity 0: Odorless
Intensity 1: Slight odor
Intensity 2: Weak odor
Intensity 3: Easily perceptible odor
Intensity 4: Strong odor
Intensity 5: Very strong odor In the group recognized to have apocrine odor of intensity 3 or more (Subject identification Nos. A to D), the detected amount of 3-hydroxy-3-methylhexanoic acid was within the scope of 15.71 to 64.29 μg. In the group recognized to have apocrine odor of intensity 1 or 2 (Subject identification Nos. E to G), the detected amount of 3-hydroxy-3-methylhexanoic acid was within the scope of 0.87 to 1.71 μg. On the contrary, in the group recognized to have no apocrine odor (intensity 0) (Subject identification Nos. H to J), 3-hydroxy-3-methylhexanoic acid was not detected from any test subjects.

Example D

The methanol fraction obtained in Example C (1 μL was used for the GC-MS analysis) was concentrated to 0.5 mL and transferred to a test tube equipped with a screw cock (NR-10, manufactured by Maruemu). 100 μL of 20 mM 2-nitrophenylhydrazine solution prepared by using 40 mM hydrochloric acid-hydrochloric acid ethanol (3:1, v/v), 100 μL of 3v/v % pyridine in ethanol solution and 100 μL of 250 mM EDC (1-ethyl-3-(3-dimethylaminopropyl)carbodiimide) in ethanol solution were successively added. A blank sample for comparing hue (0.5 mL of methanol was added) was similarly prepared. After the mixtures were heated at 60° C. for 20 minutes, 50 μL of 15% (W/V)potassium hydroxide solution prepared by water-methanol (1:4, v/v) mixture was added followed by heating at 60° C. until the brown color of the blank disappears (for 15 minutes). After cooling down to ambient temperature, the colors of reacted solutions were observed by the naked eye.

The results are shown in Table 4. The blank sample exhibited bright yellow color originated from unreacted reagent. On the other hand, the methanol fractions of the test subjects in which 3-hydroxy-3-methylhexanoic acid was detected exhibited magenta color due to production of acid hydrazide. The hue changed proportionally to the detected amount from brownish yellow to dark magenta.

TABLE 4

| Subject identification No. | Intensity of apocrine odor | Detected amount of 3-hydroxy-3-methyhexanoic acid (μg) | Color change | Hue of test solution |
| --- | --- | --- | --- | --- |
| A | 4 | 33.93 | ○ | Dark magenta |
| B | 5 | 64.29 | ○ | Very dark magenta |
| C | 3 | 15.71 | ○ | Slightly dark sienna |
| D | 4 | 37.5 | ○ | Dark magenta |
| E | 2 | 1.71 | ○ | Slightly brownish yellow |
| F | 1 | 0.87 | ○ | Slightly brownish yellow |
| G | 2 | 1.39 | ○ | Slightly brownish yellow |
| H | 0 | Not Detected | X | Light yellow(on a |
| I | 0 | " | X | level with blank) |
| J | 0 | " | X | |

<The Criteria of Evaluation>

○: The change of hue was recognized adequately

Δ: The change of hue was recognized

×: The change of hue was not recognized (on a level with the blank)

In the group recognized to have apocrine odor of intensity 3 or more, the color of the reacted solution was within the scope of red to magenta. In the group recognized to have apocrine odor of intensity 1 or 2, the color of the reaction solution was brownish yellow. On the contrary, in the group recognized to have no apocrine odor (intensity 0), the test solution of all test subjects were not colored and the hue was on a level with the blank sample.

Next, the hue of test solutions was quantified using the colorimeter. The hue was graphed by selecting the color difference (ΔE*ab) on the vertical axis, and the organoleptic test result of apocrine odor in Example C on the horizontal axis.

Figure 11:
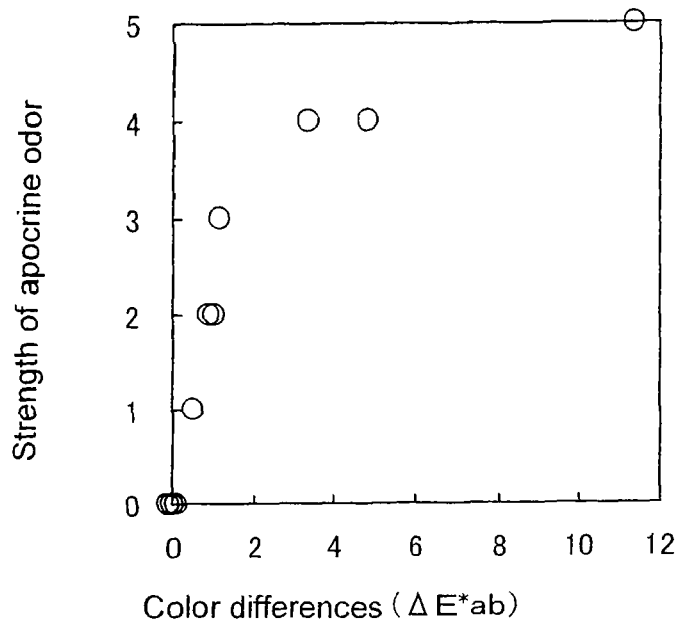
FIG. 11 shows the relationship between the strength of apocrine odor (organoleptic test) and the color differences of test solutions after color reactions.

The result was, as shown in FIG. 11, the color difference (ΔE*ab) increased proportional to the intensity of apocrine odor.

<Conditions for Measurement by Colorimeter>

Equipment: Colorimeter CT-310 (manufactured by Minolta Co., Ltd.)

Cell optical length: 2 mm

Temperature: 23° C.

The color difference was obtained from the following expression using the measured data of the blank sample as the color-difference standard color ($L^*_t$, $a^*_t$, $b^*_t$) and the measured data as (L, a*, b*):

$$\Delta E^*ab = \sqrt{((\Delta L^*)^2 + (\Delta a^*)^2 + (\Delta b^*)^2)}$$ Expression 1 wherein $\Delta L^* = L^* - L_t$
$\Delta a^* = a^* - a_t$
$\Delta b^* = b^* - b_t$ Example E 1 mL of the diethyl ether fraction obtained in Example C was transferred to a test tube equipped with a screw cock (NR-10, manufactured by Maruemu). After the solvent was removed in a water bath of 45° C. and 0.5 mL of methanol was added, the test solutions as well as a blank sample for comparing hue (0.5 mL of methanol was added) were subject to the coloration test in the manner similar to Example D using a coloration reagent. Together with the methanol fraction obtained in Example D, the hue was quantified by means of an ultraviolet-visible spectrometer. The data was graphed by selecting the absorbance of the methanol fraction on the vertical axis, and the absorbance of the ether fraction on the horizontal axis to evaluate a level of contribution of apocrine odor and acid odor to each test subject.

Figure 12:
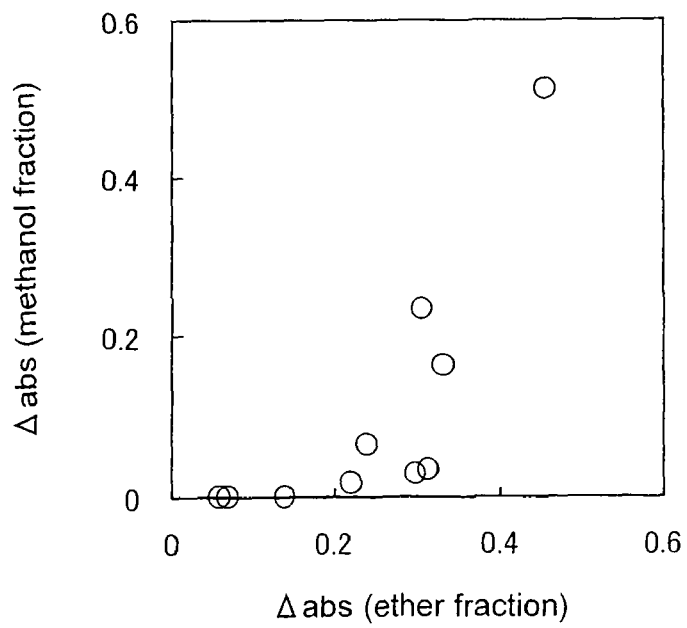
FIG. 12 shows the absorbance of methanol fraction and ether fraction after color reactions.

The result was, as shown in FIG. 12, a person whose methanol fraction of the acid extract exhibits strong color, i.e. a person recognized to have apocrine odor, tends to have the diethyl ether fraction which exhibits strong coloration (absorption). On the contrary, a person recognized to have no apocrine odor, i.e. a person whose methanol fraction does not exhibit color tends to have the diethyl ether fraction which exhibits weak coloration (absorption).

<Conditions for Measurement by Ultraviolet-Visible Spectrometer>

Equipment: BECHMAN DU-600

Cell optical length: 10 mm

Temperature: 23° C.

Measurement method of data: Peak area was measured by deducting the absorption spectrum of the blank sample from the absorption spectrum of a sample at 530 nm.

Example F

10 Test subjects of Example C were test subjects for Example F. The methanol fraction of acid extract of perspiration separated in the manner similar to Example C was concentrated to 0.5 mL, and thereafter transferred to a test tube. Together with a blank sample (0.5 mL of methanol was added) for comparing hue, 25 μL of 1.0% 9-anthryldiazomethane in acetone solution was added to each sample. The each sample was sealed and left for about 1 hours at ambient temperature. Then, using an ultraviolet lamp (manufactured by Ultraviolet Corporation, long wavelength type of 365 nm), the emitted fluorescence was observed by the naked eye. A result is shown in Table 5.

TABLE 5

| Subject identification No. | Intensity of apocrine odor | Color change | Fluorescence of test solution |
|---|---|---|---|
| A | 4 | ○ | Very strong |
| B | 5 | ○ | Very strong |
| C | 3 | ○ | Slightly strong |
| D | 4 | ○ | Very strong |
| E | 2 | ○ | Strong |
| F | 1 | ○ | Strong |
| G | 2 | ○ | Strong |
| H | 0 | X | Weak(on a level with blank) |
| I | 0 | X | |
| J | 0 | X | |

As a result shown in Table 5, the samples of test subjects recognized to have apocrine odor in Example C emitted stronger fluorescence proportional to the intensity of the apocrine odor. On the contrary, a strong fluorescence was not observed regarding the blank sample.

What we claim is:

1. A method of assessing body odor using as an index an indicator material comprising at least one member selected from the group consisting of the substances (C) and (D)
    a substance (C) which is an alcohol compound having a mercapto group at the 3-position represented by the following formula (2):

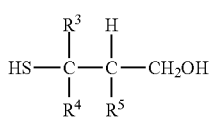

Formula (2)

wherein R3 is a hydrogen atom or methyl group; R4 is an alkyl group having 1 to 3 carbons; and R5 is a hydrogen atom or a methyl group, the total number of carbons in the formula (2) is 8 or less; and
    a substance (D) which is a derivative of an alcohol compound having a mercapto group at the 3-position, wherein an atom(s) or an atom group(s) is introduced to a mercapto group and/or a hydroxyl group of an alcohol compound having a mercapto group at the 3-position represented by the formula (2)
    said method comprising measuring the amount and the presence of said substance in a sample obtained from an axillary region of a subject and
    assessing said body odor by comparing the amount and the presence of said indicator material to a standard data obtained preliminarily;
    the standard data indicating that the presence of said indicator material in the sample represents an apocrine odor and the absence of said indicator material in the sample represents a lack of apocrine odor.

2. The method of claim 1, wherein said indicator material further comprises a substance (B) which is a derivative of β-hydroxycarboxylic acid, wherein an atom(s) or an atomic group(s) is introduced to a hydroxyl group and/or a carboxylic group of a β-hydroxycarboxylic acid compound represented by the formula (1)

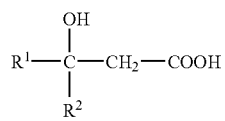

Formula (1)

wherein R$^1$ is an alkyl having 1 to 4 carbons; R$^2$ is a hydrogen atom or an alkyl having 1 to 4 carbons, and the total number of carbons in the formula (1) is 10 or less.

3. The method of claim 1, wherein the indicator material further comprises a substance (A) which is a β-hydroxycarboxylic acid compound represented by the following formula (1):

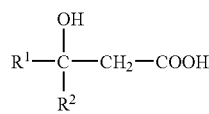

Formula (1)

wherein R$^1$ is an alkyl having 1 to 4 carbons; R$^2$ is a hydrogen atom or an alkyl having 1 to 4 carbons, and the total number of carbons in the formula (1) is 10 or less.

4. The method of claim 1, wherein the indicator material comprises the substance (C).

5. The method of claim 1, wherein the indicator material comprises the substance (D).

6. The method of claim 1, wherein the indicator material comprises the substance (C) and the substance (D).

7. The method of claim 2, wherein the indicator material comprises the substance (B), the substance (C), and the substance (D).

8. The method of claim 2, wherein the indicator material comprises the substance (B) and the substance (C).

9. The method of claim 2, wherein the indicator material comprises the substance (B) and the substance (D).

10. The method of claim 3, wherein the indicator material comprises the substance (A), the substance (C), and the substance (D).

11. The method of claim 10, wherein in the indicator material the weight ratio of the substances (C) and (A) (substance (C):substance (A)) is 1:10 to 1:1,000.

12. The method of claim 3, wherein the indicator material comprises the substance (A) and the substance (C).

13. The method of claim 12, wherein in the indicator material the weight ratio of the substances (C) and (A) (substance (C):substance (A)) is 1:10 to 1:1,000.

14. The method of claim 3, wherein the indicator material comprises the substance (A) and the substance (D).

15. The method of claim 3, wherein said indicator material further comprises a substance (B) which is a derivative of β-hydroxycarboxylic acid, wherein an atom(s) or an atomic group(s) is introduced to a hydroxyl group and/or a carboxylic group of a β-hydroxycarboxylic acid compound represented by the formula (1)

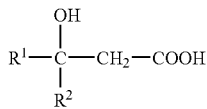
Formula (1)

wherein $R^1$ is an alkyl having 1 to 4 carbons; $R^2$ is a hydrogen atom or an alkyl having 1 to 4 carbons, and the total number of carbons in the formula (1) is 10 or less.

16. The method of claim 15, wherein the indicator material comprises the substance (A), the substance (B), the substance (C), and the substance (D).

17. The method of claim 16, wherein in the indicator material the weight ratio of the substances (C) and (A) (substance (C):substance (A)) is 1:10 to 1:1,000.

18. The method of claim 15, wherein the indicator material comprises the substance (A), the substance (B), and the substance (C).

19. The method of claim 18, wherein in the indicator material the weight ratio of the substances (C) and (A) (substance (C):substance (A)) is 1:10 to 1:1,000.

20. The method of claim 15, wherein the indicator material comprises the substance (A), the substance (B), and the substance (D).

21. A method of assessing body odor comprising steps of: incubating perspiration originated from a human in an environment with an oxygen concentration of 10 v/v % or less to produce an alcohol compound having a mercapto group at the 3-position represented by the formula (2) or an alcohol compound having a mercapto group at the 3-position, wherein an atom(s) or an atom group(s) is introduced to a mercapto group and/or a hydroxyl group of an alcohol compound having a mercapto group at the 3-position represented by the formula (2);

said method further comprising measuring the amount and the presence of said alcohol in the perspiration and assessing said body odor by comparing the amount and the presence of said alcohol to a standard data obtained preliminarily;

the standard data indicating that the presence of said alcohol in the sample represents an apocrine odor and the absence of said alcohol in the sample represents a lack of apocrine odor:

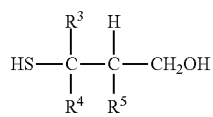
Formula (2)

wherein R3 is a hydrogen atom or methyl group; R4 is an alkyl group having 1 to 3 carbons; and R5 is a hydrogen atom or a methyl group, the total number of carbons in the formula (2) is 8 or less.

* * * * *